United States Patent
Haas et al.

(10) Patent No.: US 9,328,341 B2
(45) Date of Patent: May 3, 2016

(54) METHODS OF MODULATING UBIQUITIN LIGASE ACTIVITY

(71) Applicants: Arthur L. Haas, New Orleans, LA (US); Virginia P. Ronchi, New Orleans, LA (US)

(72) Inventors: Arthur L. Haas, New Orleans, LA (US); Virginia P. Ronchi, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 14/685,865

(22) Filed: Apr. 14, 2015

(65) Prior Publication Data
US 2015/0210998 A1 Jul. 30, 2015

Related U.S. Application Data

(63) Continuation-in-part of application No. PCT/US2013/064782, filed on Oct. 14, 2013.

(60) Provisional application No. 61/717,228, filed on Oct. 23, 2012.

(51) Int. Cl.
*C12N 9/00* (2006.01)
*C12N 9/99* (2006.01)
*A61K 31/165* (2006.01)

(52) U.S. Cl.
CPC .............. *C12N 9/99* (2013.01); *A61K 31/165* (2013.01); *C12Y 603/02019* (2013.01)

(58) Field of Classification Search
CPC ........................................................ C12N 9/93
USPC ......................................................... 435/15
See application file for complete search history.

(56) References Cited

FOREIGN PATENT DOCUMENTS

WO 2005110391 A2 11/2005

OTHER PUBLICATIONS

Chan A, et al. c-Abl Phosphorylates E6AP and Regulates its E3 Ubiquitin Ligase Activity. Biochemistry 2013 vol. 52 (18) 3119-3129.
Chan A, et al. c-Abl Phosphorylates E6AP and Regulates its E3 Ubiquitin Ligase Activity—Supporting Information. Biochemistry 2013 pp. 1-7.
Huang, L et al. Structure of an E6AP-UbcH7 complex: Insights into ubiquitination by the E2-E3 enzyme cascade. Science. 1999. vol. 286 (5443) 1321-132.
Kao Wynn H et al. Human papillomavirus type 16 E6 induces self-ubiquitination of the E6AP ubiquitin-protein ligase. Journal of Virology, 2000, vol. 74 (14) 6408-6417.
D'Abramo CM et al. Small molecule inhibitors of human papillomavirus protein-protein interactions. The Open Virology Journal 2011, vol. 5, pp. 80-95.
Matentzoglu K et al. Ubiquitin ligase E6-AP and its role in human disease. Biochemical Society Transactions 2008. vol. 36(5) 797-801.
Beaudenon S et al. HPV E6. E6AP and cervical cancer. BMC Biochemistry 2008 vol. 9 (Suppl 1) S4.
Shirakura M et al. E6AP ubiquitin ligase mediates ubiquitylation and degradation of hepatitis C virus core protein. Journal of Virology 2007, vol. 81(3) 1174-1185.
Baboshina & Haas (1996) Novel Multiubiquitin Chain Linkages Catalyzed by the Conjugating Enzymes E2EPF and RAD6 Are Recognized by 26 S Proteasome Subunit 5. J. Biol, Chem. 271, 2823-2831.
Baboshina et al., (2001) N-end Rule Specificity within the Ubiquitin/Proteasome Pathway Is Not an Affinity Effect. J. Biol. Chem. 276: 39428-39437.
Be et al., (2001) Solution Structure Determination and Mutational Analysis of the Papillomavirus E6 Interacting Peptide of E6AP. Biochemistry 40: 1293-1299.
Beer-Romero et al., (1997) Antisense targeting of E6AP elevates p53 in HPV-infected cells but not in normal cells. Oncogene 14: 595-602.
Chen et al., (1998) Identification of an alpha Helical Motif Sufficient for Association with Papillomavirus E6. J. Biol. Chem. 273: 13537-13544.
Clayton-Smith & Laan (2003) Angelman Syndrome: a review of the clinical and genetic aspects. J. Med. Genet. 40: 87-95.
Cooper et al., (2004) Biochemical Analysis of Angelman Syndrome-associated Mutations in the E3 Ubiquitin Ligase E6-associated Protein.J. Biol. Chem. 279: 41208-41217.
Dagli et al., (2012) Molecular and Clinical Aspects of Angelman Syndrome. Mol. Syndromol. 2: 100-112.
Elston et al., (1998) The identification of a conserved binding motif within human papillomavirus type 16 E6 binding peptides, E6AP and E6BPJ. Gen. Virol. 79: 371-374.
Fang et al., (1999) The spectrum of mutations in UBE3A causing Angelman Syndrome. Hum. Mol. Genet. 8: 129-135.
Flashner et al., (2013) Epigenetic Factors and Autism Spectrum Disorders. Neuromolecular Med. 15: 339-350.
Glessner et al., (2009) Autism genome-wide copy number variation reveals ubiquitin and neuronal genes. Nature 459: 569-573.

(Continued)

*Primary Examiner* — Maryam Monshipouri
(74) *Attorney, Agent, or Firm* — Thomas | Horstemeyer, LLP

(57) ABSTRACT

Methods are provided for modulating the activity of multimeric ubiquitin-protein E3 ligases including, but not limited to, E6AP ligase activities. The methods reduce the level of oligomer formation such as homotrimeric E6AP ligase to reduce the enzyme activity. Alternatively, agents are provided that can promote the association of the ligase monomers, thereby increasing the ligase activity. Accordingly, novel therapeutic strategies are provided that are useful for the treatment of pathologies resulting from mutations in the genes encoding the ligases and which adversely increase or decrease a ubiquitination reaction.

3 Claims, 15 Drawing Sheets

(56) References Cited

OTHER PUBLICATIONS

Greer et al., (2010) The Angelman Syndrome-associated ubiquitin ligase Ube3A regulates synapse development by ubiquitinating Arc. Cell 140: 704-716.

Gregianin et al., (2013) A novel SACS mutation results in non-ataxic spastic paraplegia and peripheral neuropathy. Eur. J. Neurol. 20: 1486-1491.

Haas & Bright (1988) The Resolution and Characterization of Putative Ubiquitin Carrier Protein Isozymes from Rabbit Reticulocytes. J. Biol. Chem. 263: 13258-13267.

Haas & Rose (1982) The Mechanism of Ubiquitin Activating Enzyme. J. Biol. Chem. 257: 10329-10337.

Haas A. L. (2005) Purification of E1 and E1-Like Enzymes. Methods Mol. Biol. 301: 23-35.

Haupt et al., (1997) Mdm2 Promotes the Rapid Degradation of p53. Nature 387: 296-299.

Heer et al., (2011) E6*, the 50 Amino Acid Product of the Most Abundant Spliced Transcript of the E6 Oncoprotein in High-Risk Human Papillomavirus, Is a Promiscuous Folder and Binder. Biochemistry 50, 1376-1383.

Medcalf & Milner (1993) Targeting and Degradation of p53 by E6 of human papillomavirus type 16 is perferential for the 1620+ p53 conformation. Oncogene 8: 2847-2851.

Huang et al., (2013) Behavioral deficits in an Angelman syndrome model: Effects of genetic background and age. Behav. Brain Res. 243: 79-90.

Huibregtse et al., (1991) A cellular protein mediates association of p53 with the E6 oncoprotein of human papillomavirus types 16 or 18. EMBO J. 10: 4129-4135.

Huibregtse et al., (1993) Localization of the E6-AP Regions That Direct Human Papillomavirus E6 Binding, Association with p53, and Ubiquitination of Associated Proteins. Mol. Cell Biol. 13: 4918-4927.

Huibregtse et al., (1995) A family of proteins structurally and functionally related to the E6-AP ubiquitin-protein ligase. Proc. Natl. Acad. Sci. U.S.A. 92: 2563-2567.

Jiang et al., (1999) Genetics of Angelman Syndrome. Am. J. Hum. Genet. 65: 1-6.

Kamadurai et al., (2009) Insights into ubiquitin transfer cascades from a structure of a UbcH5B~Ubiquitin-HECTNEDD4L complex. Mol. Cell 36: 1095-1102.

Maspero et al., (2011) Structure of the HECT:ubiquitin complex and its role in ubiquitin chain elongation. EMBO Rep. 12: 342-349.

Kentsis et al., (2002) Control of biochemical reactions through supramolecular RING domain self-assembly. Proc. Natl. Acad. Sci. U.S.A. 99: 15404-15409.

Kishino et al., (1997) UBE3A/E6-AP mutations cause Angelman syndrome. Nat. Genet. 15: 70-73.

Kiyono et al., (1998) Both Rb/p16INK4a inactivation and telomerase activity are required to immortalize human epithelial cells. Nature 396: 84-88.

Krissinel & Henrick (2007) Inference of Macromolecular Assemblies from Crystalline State. J. Mol. Biol. 372, 774-797.

Kühnle et al., (2013) Role of the ubiquitin ligase E6AP/UBE3A in controlling levels of the synaptic protein Arc. Proc. Natl. Acad. Sci. U.S.A. 110: 8888-8893.

Lawson et al., (2009) Koilocytes indicate a role for human papilloma virus in breast cancer. Br. J. Cancer 101, 1351-1356.

Levy & Teichmann (2013) Structural, Evolutionary, and Assembly Principles of Protein Oligomerization. Prog. Mol. Biol. Transl. Sci. 117: 25-51.

Liu et al., (2009) Determinants of Stability for the E6 Protein of Papillomavirus Type 16. J. Mol. Biol. 386: 1123-1137.

Lossie et al., (2001) Distinct phenotypes distinguish the molecular classes of Angelman syndrome. J. Med. Genet. 38: 834-845.

Mabb et al., (2011) Angelman Syndrome: Insights into Genomic Imprinting and Neurodevelopmental Phenotypes. Trends Neurosci. 34: 293-303.

Margolis et al., (2010) EphB-mediated degradation of the RhoA GEF Ephexin5 relieves a developmental brake on excitatory synapse formation. Cell 143: 442-455.

Marianayagam et al., (2004) The power of two: protein dimerization in biology. Trends Biochem. Sci. 29: 618-625.

Matsuura et al., (1997) De novo truncating mutations in E6-AP ubiquitin-protein ligase gene (UBE3A) in Angleman syndrome. Nat. Genet. 15: 74-77.

Muench et al., (2010) Cutaneous Papillomavirus E6 Proteins Must Interact with p300 and Block p53-Mediated Apoptosis for Cellular Immortalization and TumorigenesisCancer Res. 70: 6913-6924.

Munakata et al., (2007) Hepatitis C Virus Induces E6AP-Dependent Degradation of the Retinoblastoma Protein. PLoS Pathog. 3: 1335-1347.

Nicholls & Knepper (2001) Genome Organization, Function, and Imprinting in Prader-Willi and Angelman SyndromesAnnu. Rev. Genomics Hum. Genet 2: 153-175.

Nominé et al., (2003) Domain Substructure of HPV E6 Oncoprotein: Biophysical Characterization of the E6 C-Terminal DNA-Binding Domain. Biochemistry 42: 4909-4917.

Ogunjimi et al., (2010) The Ubiquitin Binding Region of the Smurf HECT Domain Facilitates Polyubiquitylation and Binding of Ubiquitylated Substrates. J. Biol. Chem. 285: 6308-6315.

Page & Jencks (1971) Entropic Contributions to Rate Accelerations in Enzymic and Intramolecular Reactions and the Chelate Effect. Proc. Natl. Acad. Sci. U.S.A. 68: 1678-1683.

Pandya et al., (2010) A Structural Element within the HUWE1 HECT Domain Modulates Self-ubiquitination and Substrate Ubiquitination Activities. J. Biol. Chem. 285: 5664-5673.

Perica et al., (2012) Angelman syndrome: advancing the research frontier of neurodevelopmental disorders. Evolution of oligomeric state through geometric coupling of protein interfaces. Proc. Natl. Acad. Sci. U.S.A. 109: 8127-8132.

Philpot et al., (2011) Angelman syndrome: advancing the research frontier of neurodevelopmental disorders. J. Neurodev. Disord. 3: 50-56.

Ronchi & Haas (2012) Measuring Rates of Ubiquitin Chain Formation as a Functional Readout of Ligase Activity. Methods Mol. Biol. 832: 197-218.

Ronchi et al., (2013) E6AP/UBE3A Ubiquitin Ligase Harbors Two E2~ubiquitin Binding Sites. J. Biol. Chem. 88: 10349-10360.

Rotin & Kumar (2009) Physiological functions of the HECT family of ubiquitin ligases. Nat. Rev. Mol. Cell Biol. 10, 398-409.

Samaco et al., (2005) Epigenetic overlap in autism-spectrum neurodevelopmental disorders: MECP2 deficiency causes reduced expression of UBE3A and GABRB3. Hum. Mol. Genet. 14: 483-492.

Sato & Stryker (2010) Genomic imprinting of experience-dependent cortical plasticity by the ubiquitin ligase gene Ube3a. Proc. Natl. Acad. Sci. U.S.A. 107: 5611-5616.

Schaaf et al., (2011) Oligogenic heterozygosity in individuals with high-functioning autism spectrum disorders. Hum. Mol. Genet. 20: 3366-3375.

Scheffner et al., (1990) The E6 Oncoprotein Encoded by Human Papillomavirus Types 16 and 18 Promotes the Degradation of p53. Cell 63: 1129-1136.

Scheffner et al., (1993) The HPV-16 E6 and EG-AP Complex Functions as a Ubiquitin-Protein Ligase in the Ubiquitination of p53. Cell 75: 495-505.

Scheffner et al., (1994) The HPV-16 E6 and EG-AP Complex Functions as a Ubiquitin-Protein Ligase in the Ubiquitination of p53. Proc. Natl. Acad. Sci. U.S.A. 91: 8797-8801.

Siepmann et al., (2003) Protein Interactions within the N-end Rule Ubiquitin Ligation Pathway. J. Biol. Chem. 278: 9448-9457.

Smith et al., (2011) Increased Gene Dosage of Ube3a Results in Autism Traits and Decreased Glutamate Synaptic Transmission in Mice. Sci. Transl. Med. 3: 103ra97.

Spitkovsky et al., (1996) p53-independent growth regulation of cervical cancer cells by the papilloma virus E6 oncogene. Oncogene 13: 1027-1035.

Streich et al., (2013) Tripartite Motif Ligases Catalyze Polyubiquitin Chain Formation through a Cooperative Allosteric Mechanism. J. Biol. Chem. 288: 8209-8221.

(56) References Cited

OTHER PUBLICATIONS

Sun et al., (2004) The TRAF6 Ubiquitin Ligase and TAK1 Kinase Mediate IKK Activation by BCL10 and MALT1 in T Lymphocytes. Mol. Cell 14: 289-301.

Sutcliffe et al., (1997) The E6-AP Ubiquitin-Protein Ligase (UBE3A) Gene Is Localized within a Narrowed Angelman Syndrome Critical Region. Genome Res. 7: 368-377.

Talis et al., (1998) The Role of E6AP in the Regulation of p53 Protein Levels in Human Papillomavirus (HPV)-positive and HPV-negative Cells. J. Biol. Chem. 273: 6439-6445.

Tokgöz et al., (2012) E1-E2 Interactions in Ubiquitin and Nedd8 Ligation Pathways. J. Biol. Chem. 287: 311-321.

van Woerden et al., (2007) Rescue of neurological deficits in a mouse model for Angelman syndrome by reduction of alpha CaMKII inhibitory phosphorylation. Nat. Neurosci. 10: 280-282.

Verdecia et al., (2003) Conformational Flexibility Underlies Ubiquitin Ligation Mediated by the WWP1 HECT Domain E3 Ligase. Mol. Cell 11: 249-259.

Wang & Pickart (2005) Different HECT domain ubiquitin ligases employ distinct mechanisms of polyubiquitin chain synthesis. EMBO J. 24: 4324-4333.

Wang et al., (2006) Molecular determinants of polyubiquitin linkage selection by an HECT ubiquitin ligase. EMBO J. 25: 1710-1719.

Williams et al., (2006) Angelman Syndrome 2005: Updated Consensus for Diagnostic Criteria. Am. J. Med. Genet. A 140: 413-418.

Yashiro et al., (2009) Ube3a is required for experience-dependent maturation of the neocortex. Nat. Neurosci. 12: 777-783.

Zanier et al., (2005) Kinetic Analysis of the Interactions of Human Papillomavirus E6 Oncoproteins with the Ubiquitin Ligase E6AP Using Surface Plasmon Resonance. J. Mol. Biol. 349: 401-412.

Zanier et al., (2010) E6 Proteins from Diverse Papillomaviruses Self-Associate Both In Vitro and In Vivo. J. Mol. Biol. 396: 90-104.

Zanier et al., (2013) Structural basis for hijacking of cellular LxxLL motifs by papillomavirus E6 oncoproteins. Science 339: 694-698.

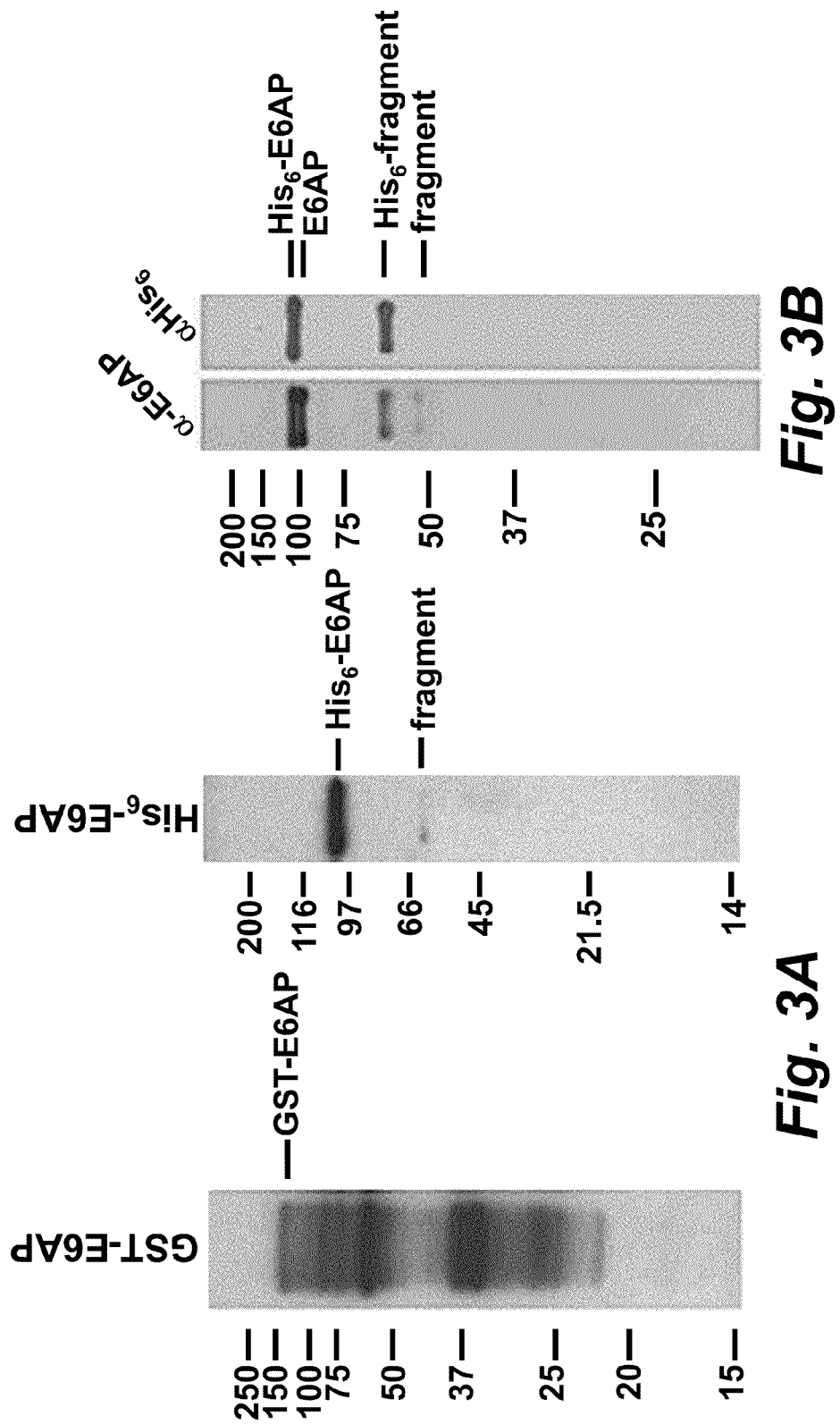

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial equence
<220> FEATURE:
<223> OTHER INFORMATION: N-acetylated peptide residues 474-490 of E6AP
      ligase isoform 1
<220> FEATURE:
<221> NAME/KEY: MOD_RES
<222> LOCATION: (1)..(1)
<223> OTHER INFORMATION: ACETYLATION

<400> SEQUENCE: 1

Asn Arg Ile Arg Met Tyr Ser Glu Arg Arg Ile Thr Val Leu Tyr Ser
1               5                   10                  15

Leu
```

METHODS OF MODULATING UBIQUITIN LIGASE ACTIVITY

CROSS-REFERENCE TO RELATED APPLICATIONS

This application is a Continuation-in-Part of the 35 U.S.C. §371 national stage of PCT application PCT/US 2013/064782 "BLOCKING ACTIVITIES OF E6AP LIGASE" filed on Oct. 14, 2013, which claims priority to and the benefit of U.S. Provisional Application 61/717,228 titled "BLOCKING ACTIVITIES OF E6AP LIGASE" filed Oct. 23, 2012, the entire disclosures of which are incorporated herein by reference.

STATEMENT REGARDING FEDERALLY SPONSORED RESEARCH OR DEVELOPMENT

This invention was made with government support under grant GM034009 awarded by the National Institutes of Health. The government has certain rights in the invention.

TECHNICAL BACKGROUND

The present disclosure relates generally to methods of modulating the multimeric structure of an E6AP ligase protein. In particular, the disclosure relates to the use of small molecule non-competitive inhibitors to disrupt E6AP ligase oligomerization, reducing E6AP ligase activity, or the use of peptide agents that induce oligomerization of E6AP monomers. The disclosure further relates to use of such modulating agents as therapeutic agents for modulating E6AP-related pathologies.

SEQUENCE LISTING

The present disclosure includes a sequence listing incorporated herein by reference in its entirety.

BACKGROUND

Ubiquitin, a small regulatory protein found in all tissues of eukaryotic organisms, is involved in numerous cellular processes including protein degradation and the cell cycle, through conjugation of ubiquitin to other proteins. Ubiquitin is conjugated to other proteins (ubiquitination) by an enzymatic, post-translational modification of a target protein, as shown schematically in FIG. 1, involving a series of steps. The ubiquitin is first activated by an E1 ubiquitin-activating protein. Activated ubiquitin is then transferred from the E1 ubiquitin-activating protein to an E2 ubiquitin-conjugating enzyme. Finally, the cascade creates a bond between ubiquitin and the target protein. The final step generally requires the activity of an E3 ubiquitin-protein ligase.

E6AP is the founding member of the Hect (Homologous to E6-associated protein ligase Carboxy Terminus) ubiquitin ligase family and is defined by a highly conserved 350-residue C-terminal catalytic domain (Huibregtse et al., (1995) Proc. Natl. Acad. Sci. U.S.A. 92: 2563-2567; Rotin & Kumar (2009) Nat. Rev. Mol. Cell Biol. 10, 398-409). The Hect domain is characterized by the presence of an active site cysteine that forms an obligatory high energy thioester bond with ubiquitin prior to transfer of the latter to specific substrate proteins, the identity of which is defined by the N-terminal targeting domain (Rotin & Kumar (2009) Nat. Rev. Mol. Cell Biol. 10, 398-409). The E6AP ligase Hect domain assembles Lys48-linked polyubiquitin degradation signals that are recognized by the 26 S proteasome (Wang & Pickart (2005) EMBO J. 24: 4324-4333; Wang et al., (2006) EMBO J. 25: 1710-1719).

Both activation and loss of E6AP ligase function are implicated in various human diseases, as discussed elsewhere (Beaudenon & Huibregtse (2008) BMC Biochem. 9: S4; Flashner et al., (2013) Neuromolecular Med. 15: 339-350; Nicholls & Knepper (2001) Annu. Rev. Genomics Hum. Genet. 2: 153-175). Abrogation of E6AP ligase function by deletion, imprinting defects, or mutation of the UBE3A gene locus within the 15q11-13 chromosome region is associated with the neurological disorder Angelman syndrome (Matentzoglu & Scheffner (2008) Biochem. Soc. Trans. 36: 797-801; Kishino et al., (1997) Nat. Genet. 15: 70-73; Sutcliffe et al., (1997) Genome Res. 7: 368-377). Patients affected with Angelman syndrome are characterized by severe intellectual and developmental disability, speech impairment, behavioral uniqueness, epilepsy, and severely abnormal electroencephalography, among other symptoms (Mabb et al., (2011) Trends Neurosci. 34: 293-303; Matsuura et al., (1997) Nat. Genet. 15: 74-77; Lossie et al., (2001) J. Med. Genet. 38: 834-845; Williams et al., (2006) Am. J. Med. Genet. A 140: 413-418).

Most of the naturally occurring mutations within the UBE3A gene introduce deletions that generate truncated forms of E6AP ligase lacking the intact Hect domain; however, approximately 10% of the genetic alterations correspond to point mutations within the E6AP ligase coding region (Clayton-Smith & Laan (2003) J. Med. Genet. 40: 87-95; Jiang et al., (1999)Am. J. Hum. Genet. 65: 1-6). Although many of the point mutants represent loss-of-function alterations and are not able to ubiquitinate their substrate, paradoxically, many retain the ability to form a thioester bond with ubiquitin (Cooper et al., (2004) J. Biol. Chem. 279: 41208-41217). In contrast, duplication of the corresponding UBE3A gene is thought to result in some cases of autism spectrum disorder (Smith et al., (2011) Sci. Transl. Med. 3: 103ra97; Schaaf et al., (2011) Hum. Mol. Genet. 20: 3366-3375; Glessner et al., (2009) Nature 459: 569-573; Samaco et al., (2005) Hum. Mol. Genet. 14: 483-492). These observations suggest a narrow range of E6AP ligase activity for normal neurological development because UBE3A-deficient mouse models or those expressing higher levels of the ligase show phenotypes similar to Angelman syndrome or autism, respectively (Smith et al., (2011) Sci. Transl. Med. 3: 103ra97; Yashiro et al., (2009) Nat. Neurosci. 12: 777-783; Sato & Stryker (2010) Proc. Natl. Acad. Sci. U.S.A. 107: 5611-5616; Huang et al., (2013) Behav. Brain Res. 243: 79-90). In general, the clinical symptoms associated with the neurological disorders and the identified targets of E6AP-catalyzed ubiquitination localize to regulatory pathways required for synaptic plasticity (Greer et al., (2010) Cell 140: 704-716; Margolis et al., (2010) Cell 143: 442-455; Gregianin et al., (2013) Eur. J. Neurol. 20: 1486-1491; Dagli et al., (2012) Mol. Syndromol. 2: 100-112; Philpot et al., (2011) J. Neurodev. Disord. 3: 50-56). The identification of Arc and Ephexin 5 as targets of E6AP, both of which function to mediate synaptic remodeling, provide a framework for reconciling the loss-of-function mutations in the E6AP ligase maternal copy and the neurological and developmental defects present in affected individuals (Greer et al., (2010) Cell 140: 704-716; Margolis et al., (2010) Cell 143: 442-455, 30; Kühnle et al., (2013) Proc. Natl. Acad. Sci. U.S.A. 110: 8888-8893), although more recent evidence questions a role for E6AP ligase in targeting Arc degradation (Kühnle et al., (2013) Proc. Natl. Acad. Sci. U.S.A. 110: 8888-8893).

Due to its role in various pathologies, therefore, methods and therapies are needed to regulate E6AP ligase activities and either block the catalytic actions of E6AP ligase in pathologies involving overactive E6AP ligase, or increase E6AP ligase activity where pathologically deficient.

SUMMARY

Kinetic and biophysical methods have now been used to demonstrate for the first time that an E6AP ligase oligomer is the catalytically competent form of the enzyme. Based on an earlier structure for E6AP ligase initially discounted as an artifact of crystal packing forces (Huang et al., (1999) *Science* 286: 1321-1326), it is contemplated that the fully functional form of the oligomer is a trimer, computational analysis of which allowed the identification of conserved residues located at the subunit interfaces. Using rates of $^{125}$I-polyubiquitin chain assembly as a functional readout, a subset of residues essential for stabilizing the active trimer has been identified. It has further been found that small molecule mimics of a key stabilizing interaction are sufficient to dissociate the trimer and thereby reduce E6AP-catalyzed chain assembly but not Cys$^{820}$~ubiquitin thioester formation. Such small molecule mimetics provide a means to modulate E6AP ligase activity, not by directly regulating its enzyme catalytic activity but indirectly by promoting, or not, trimerization of the E6AP ligase subunits.

In contrast, E6 viral protein enhances E6AP ligase activity by promoting oligomerization as a consequence of the ability of the former to dimerize through its N-terminal Zn$^{2+}$ binding domain (Ronchi et al., (2013) *J. Biol. Chem.* 88: 10349-10360; Heer et al., (2011) *Biochemistry* 50: 1376-1383). Remarkably, E6-induced oligomerization rescues synthetic and Angelman syndrome loss-of-function mutations contributing to subunit association and stabilization. The current results explain previously unresolved roles for a cohort of point mutations in the neurological pathology of Angelman syndrome, reveal new strategies for regulating E6AP ligase function by modulating subunit assembly, and provide insights into the role of oligomerization in polyubiquitin chain formation by the Hect ligase superfamily.

One aspect of the disclosure encompasses embodiments of a method of modulating the activity of a ubiquitin-protein E3 ligase comprising contacting a ubiquitin-protein E3 ligase with an agent that reduces ligase oligomer formation or with an agent that increases ligase oligomer formation.

In some embodiments of this aspect of the disclosure, the oligomer can be a homooligomer of at least two ubiquitin-protein E3 ligase polypeptides.

In some embodiments of this aspect of the disclosure, the ubiquitin-protein E3 ligase can be E6AP encoded by the UBE3A gene.

In some embodiments of this aspect of the disclosure, the agent that reduces ubiquitin-protein E3 ligase oligomer formation can be a non-competitive inhibitor of ligase activity.

In some embodiments of this aspect of the disclosure, the agent is N-acetyl-L-phenylalanylamide.

In some embodiments of this aspect of the disclosure, the agent that increases ubiquitin-protein E3 ligase oligomer formation can be a peptide fragment.

In some embodiments of this aspect of the disclosure, the agent that increases ubiquitin-protein E3 ligase oligomer formation can be a peptide fragment from a human papilloma virus.

In some embodiments of this aspect of the disclosure, the agent that increases ubiquitin-protein E3 ligase oligomer formation can be an E6 polypeptide, or a peptide fragment therefrom, of a human papilloma virus.

In some embodiments of this aspect of the disclosure, the E6AP can comprise a mutated amino acid residue or residues that result in a pathological condition in a human or animal subject.

BRIEF DESCRIPTION OF THE DRAWINGS

Aspects of the present disclosure will be more readily appreciated upon review of the detailed description of its various embodiments, described below, when taken in conjunction with the accompanying drawings. The drawings are described in greater detail in the description and examples below.

FIG. 2A is a graph illustrating initial rates of E6AP-catalyzed free polyubiquitin chain formation determined in the presence of 8 nM human Uba1, 200 nM UbcH7, 0.2 nM GST-E6AP, 5 µM $^{125}$I-ubiquitin, and the indicated concentrations of recombinant-free Glutathione-S-Transferase (GST).

FIG. 2B is a digital image of an autoradiogram of $^{125}$I-ubiquitin conjugation assays performed under initial velocity conditions in the presence of 60 nM human Uba1, 400 nM UbcH7, 6 nM GST-E6AP, 4 µM $^{125}$I-ubiquitin, and either 54 µM GST-E6APΔ495 or 66 µM E6APΔ495.

FIG. 2C is a graph illustrating initial rates of $^{125}$I-ubiquitin conjugation determined in the presence of 8 nM GST-E6AP ligase and the indicated concentrations of GST-E6APΔ495. Radioactivity associated with the stacker gel representing free and unanchored $^{125}$I-polyubiquitin chains was quantitated to calculate the resulting initial velocities. The solid line represents non-linear inverse hyperbolic regression fits of the data using GraFit version 5.0.

FIG. 2D is a graph illustrating initial rates of $^{125}$I-ubiquitin conjugation determined in the presence of GST-E6AP ligase and the indicated concentrations of E6APΔ495. The solid line represents non-linear inverse hyperbolic regression fits of the data using GraFit version 5.0.

FIG. 2E is a graph illustrating initial rate assays of $^{125}$I-ubiquitin conjugation determined in the presence of the indicated concentrations of GST-HectC820A (open circles) or HectC820A (closed circles). The solid line represents non-linear inverse hyperbolic regression fits of the data using GraFit version 5.0.

FIG. 2F is a schematic diagram depicting the model for inhibition of polyubiquitin chain formation by the Δ495 truncation or free Hect domain.

FIG. 3A illustrates a SDS-PAGE analysis of selected E6AP ligase preparations. Coomassie-stained 10% (w/v) SDS-PAGE resolution of affinity-purified recombinant GST-E6AP ligase expressed in *E. coli* (left) versus His$_6$-E6AP ligase expressed in baculovirus (right). Mobility markers are shown to the left of the corresponding panels. Mobilities of selected E6AP ligase species are shown to the right of the corresponding panels.

FIG. 3B illustrates a Western blot of 12% (w/v) SDS-PAGE resolution of baculovirus-expressed His$_6$-E6AP ligase stained with anti-E6AP ligase antibody (left) and then stripped and restrained with anti-His$_6$ antibody (right). Mobility markers are shown to the left of the corresponding panels. Mobilities of selected E6AP ligase species are shown to the right of the corresponding panels.

FIG. 4A is a graph illustrating 150 µl of 75 µm full-length $His_6$-E6AP ligase analyzed in a 1×30 cm Superose 12 FPLC gel filtration column equilibrated in 50 mM Tris-HCl (pH 7.5) and 50 mM NaCl. Protein was monitored by 280 nm absorbance (filled circles), and enzyme activity was monitored by E3-limiting $^{125}$I-polyubiquitin chain formation (open circles). Inset: calibration plot with the elution position of the peak E6AP ligase activity shown with an open circle.

FIG. 4B is a graph illustrating a static light-scattering analysis of 18 µM full-length $His_6$-E6AP ligase in 50 mM Tris-HCl (pH 7.5) containing 200 mM NaCl at 37° C. The main peak of 283 kDa exhibits a polydispersity of 17%. The higher molecular weight low abundance peak of 50 nm radius represents residual aggregates not removed by Mono Q FPLC.

FIG. 4C is a graph illustrating a static light-scattering analysis in the presence of 16 µM $His_6$-E6AP ligase and 8% (v/v) methanol in the absence (solid line; 23% polydispersity) or presence (dashed line; 14% polydispersity) of 61 mM Ac-$PheNH_2$.

FIG. 5A is a graph illustrating the concentration dependence of Ac-$PheNH_2$ on the initial rate of $^{125}$I-polyubiquitin chain assembly under E6AP-limiting conditions, with the solid line representing a nonlinear inverse regression analysis fit to a hyperbolic kinetics; inset: semi-reciprocal plot of the resulting data. Incubations contained 400 nM Uba1, 200 nM UbcH7, 8.8 nM $His_6$-E6AP, 5 µM $^{125}$I-ubiquitin, and the indicated concentrations of Ac-$PheNH_2$.

FIG. 5B is a graph illustrating a double reciprocal plot of the dependence of $[UbcH7]_o$, on the initial rate of polyubiquitin chain formation in the absence (solid circles) or presence (open circles) of 44 mM Ac-$PheNH_2$. All incubations contained 5% (v/v) methanol as a carrier for the Ac-$PheNH_2$.

FIG. 6A is a graph illustrating initial rates of $^{125}$I-polyubiquitin chain assembly under E6AP-limiting conditions analyzed in the absence or presence of the indicated concentrations of N-terminal peptide and evaluated by nonlinear regression fit to an inverse hyperbolic equation. Reactions contained 34 nM Uba1, 390 nM UbcH7, 1.3 nM $His_6$-E6AP, and 4 µM $^{125}$I-ubiquitin. Inset: semi-reciprocal plot of the data.

FIG. 6B is a graph illustrating a double reciprocal plot of initial rates of $^{125}$I-polyubiquitin chain assembly under E6AP-limiting conditions in the absence (closed circles) or presence (open circles) of 32 µM N-terminal peptide. Reactions contained 33 nM Uba1, 0.6 nM $His_6$-E6AP, 4 µM $^{125}$I-ubiquitin, and the corresponding $[UbcH7]_o$, concentrations.

FIG. 6C is a graph illustrating static light-scattering spectra of 17 µM full-length $His_6$-E6AP ligase determined in the absence (solid line; 10±3% polydispersity) or presence (dashed line; 10±2% polydispersity) of 88 µM Ac-NRIRMY-SERRITVLYSL peptide (SEQ ID NO: 1).

FIG. 7A illustrates the structure of the E6AP ligase Hect domain trimer illustrating residues stabilizing the structure.

FIGS. 7B and 7C illustrate close-up views of the spatial orientation for $Tyr^{533}$, $Asp^{543}$, and $Arg^{626}$. Residues in parentheses are those previously examined (Chan et al., 2013) *Biochemistry* 52: 3119-3129).

FIG. 8A is a graph illustrating initial rates of $^{125}$I-ubiquitin polyubiquitin chain formation determined under E6AP-limiting conditions in the absence (closed circles) or presence (open circles) of 20 nM E6 protein and evaluated by nonlinear regression fit to the Michaelis-Menten equation. Assays contained 70 nM Uba1, 0.4 nM $His_6$-E6AP, 4 µM $^{125}$I-ubiquitin, and the indicated UbcH7 concentrations. Inset, double reciprocal plot of the data.

FIG. 8B is a graph illustrating double reciprocal plot of the initial rates of $^{125}$I-ubiquitin conjugation activity determined under E6AP-limiting conditions in the absence (closed circles) or presence (open circles) of 3.3 µM E6(HPV16)Δ91. Assays contained 30 nM Uba1, 1 nM $His_6$-E6AP, 4 µM $^{125}$I-ubiquitin, and the indicated UbcH7 concentrations.

FIG. 8C is a digital image of an SDS-PAGE analysis of conjugation reactions conducted with 110 nM Uba1, 480 nM UbcH7, 5 µM $^{125}$I-ubiquitin, and 1 nM wild-type or mutant GST-E6AP ligase in the absence (lanes 1-7) or presence (lanes 8-13) of 20 nM E6(HPV16).

FIG. 8D is a graph illustrating quantitation of product formation rates in the absence (open bars) or presence (black bars) of E6(HPV16). Data for wild-type GST-E6AP ligase and GST-E6APY533A are plotted on the left axis, whereas data for GST-E6APR626A, -D543A, and -F727D are plotted on the right axis.

DESCRIPTION OF THE DISCLOSURE

Figure 1:
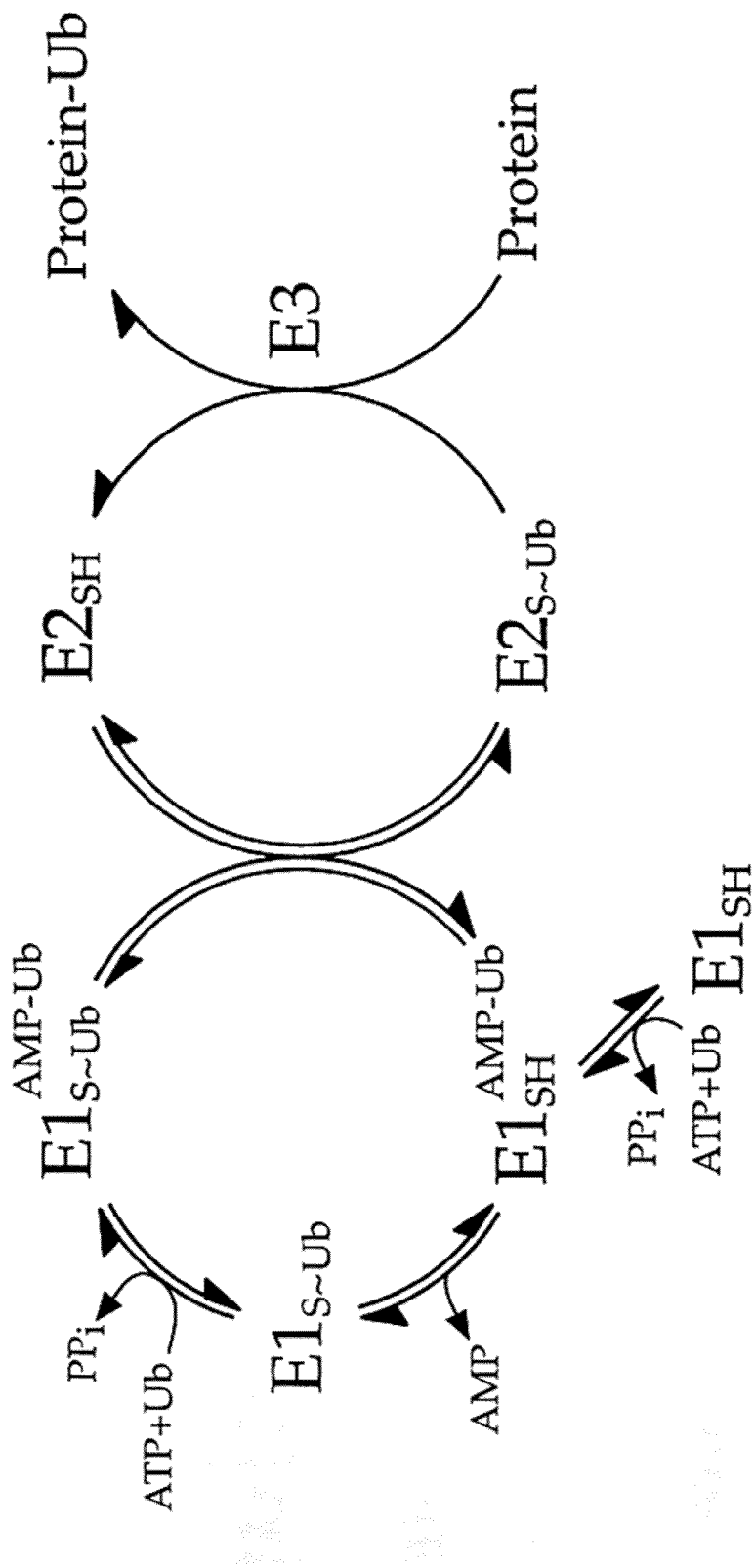
FIG. 1 illustrates a schematic mechanism of ubiquitin conjugation.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law, allowing for the presence of more than that which is recited so long as basic or novel characteristics of that which is recited is not changed by the presence of more than that which is recited, but excludes prior art embodiments.

Abbreviations

E6AP, E6-associated protein (gene name UBE3A); E6, human papilloma virus 16 E6 protein; Hect, Homologous to E6-associated protein ligase carboxy terminus; HPV, human papilloma virus; Ac-PheNH$_2$, N-acetyl-L-phenylalanylamide; E1, generic term for activating enzymes of Class 1 ubiquitin-like proteins; E2/Ubc, generic name for ubiquitin carrier protein/ubiquitin-conjugating enzyme; E3, generic name for ubiquitin:protein isopeptide ligase; UbcH7, human E2 carrier protein (gene name UBE2L3); Uba1, ubiquitin-activating enzyme (gene name UBE1); GST, glutathione-S-transferase; SDS, sodium dodecyl sufate; SDS-PAGE, sodium dodecyl sufate-polyacrylamide electrophoresis.

Definitions

The term "ubiquitin ligase (also called an E3 ubiquitin ligase)" as used herein refers to a protein that recruits an E2 ubiquitin-conjugating enzyme that has been loaded with ubiquitin, recognizes a protein substrate, and assists or directly catalyzes the transfer of ubiquitin from the E2 to the protein substrate. In the case of the Hect ligases, this reaction proceeds via the Hect domain Cys-Ub-thioster. The ubiquitin is attached to a lysine on the target protein by an isopeptide bond. E3 ligases interact with both the target protein and the E2 enzyme, and so impart target protein substrate specificity to the E2. Most commonly, E3s polyubiquitinate their substrate with Lys48-linked chains of ubiquitin, targeting the substrate for destruction by the proteasome. Ubiquitination by E3 ligases regulates diverse areas such as cell trafficking, DNA repair, and signaling. E3 ligases are also key players in cell cycle control, mediating the degradation of cyclins, as well as cyclin-dependent kinase inhibitor proteins. The human genome encodes over 600 putative E3 ligases, allowing for tremendous diversity in targeted substrates.

Ubiquitination of protein is by the overall reaction:

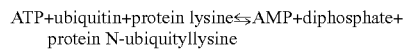

$$\text{ATP+ubiquitin+protein lysine} \rightleftharpoons \text{AMP+diphosphate+ protein N-ubiquityllysine}$$

Canonical ubiquitinylation creates an isopeptide bond between a lysine residue on a target protein and the ubiquitin C-terminal glycine 76.

The term "ubiquitin-protein ligase E3A (UBE3A) (also known as E6AP ubiquitin-protein ligase (E6AP))" as used herein refers to an enzyme that in humans is encoded by the UBE3A gene. This enzyme is involved in targeting proteins for degradation within cells, E3 ubiquitin-protein ligase (EC 6.3.2.19) catalyzing the transfer of the activated ubiquitin from the bound E2-ubiquitin to the lysine of the bound target protein or other ubiquitin molecules to make an isopeptide bond. E1 catalyzes the ATP-dependent step (as shown schematically in FIG. 1). Both copies of the UBE3A gene are active in most of the body's tissues. The UBE3A gene is located on the long (q) arm of chromosome 15 between positions 11 and 13, from base pair 23,133,488 to base pair 23,235,220.

Mutations within the UBE3A gene are responsible for some cases of Angelman syndrome. Most of these mutations result in an abnormally short, nonfunctional version of ubiquitin protein ligase E3A. Because the copy of the gene inherited from a person's father (the paternal copy) is normally inactive in the affected areas of the brain, a mutation in the remaining maternal copy prevents any of the normal enzyme from being produced in the brain. Like mutations within the gene, chromosomal changes such as deletions and rearrangements (translocations) of genetic material of the human chromosomal region 15q11-13 can prevent any functional ubiquitin protein ligase E3A from being produced in the brain.

E3 ligases are classified into four families: HECT, RING-finger, U-box, and PHD-finger. The RING-finger E3 ligases are the largest family and contain ligases such as the anaphase-promoting complex (APC) and the SCF complex. Individual E3 ubiquitin ligases include, but are not limited to, E3A, HECTD1, HECTD2, HECTD3, HECW1, HECW2, HERC1, HERC2, HERC3, HERC4, HUWE1, ITCH, UBE3A, UBE3B, UBE3C, UBE4A, and UBE4B.

The term "modulate" as used herein refers to the activity of a composition to affect (e.g., to increase or decrease (reduce) an aspect of a protein or enzyme function.

The terms "oligomer" and "multimer" as used herein are intended to be interchangeable and refer to a macromolecular complex formed by non-covalent bonding of at least two polypeptides. As used herein, the term "homo-oligomer" refers to the association of identical molecules and by contrast, a hetero-oligomer would be made of at least two different macromolecules.

The term "multimer" as used herein particularly refers to the tertiary structure of E6AP ligase that, with the wild-type E6AP ligase polypeptide as expressed from the UBE1 gene, is a trimer of three identical polypeptides and which is the catalytically active form of the E6AP.

The terms "oligomerization" and "multimerization" as used herein are intended to be interchangeable and refer to the process of converting a monomer or a mixture of monomers into an oligomer.

The term "small molecule agent" as used herein refers to any compound such as, but not limited to N-phenylalanine amide that may interact with one or more of the polypeptide subunits of an E6AP ligase to either disrupt the multimeric E6AP ligase structure or prevent the formation of such, thereby reducing the detectable activity of the E6AP ligase under in vitro or in vivo conditions.

Description

The present disclosure provides methods of modulating the activity of a ubiquitin-protein E3 ligase protein. While not wishing to be limiting in scope, the methods of the disclosure, are advantageously applied to the ubiquitin-protein E3 ligase E6AP although it is contemplated that the ability to disrupt or promote the multimerization of other ubiquitin-protein E3 ligases also will modulate their activity. It has further been found that other degrees of oligomerization than just trimerization can modulate the activity of E6A. For example, but not intending to be limiting, dimerization of the individual polypeptide monomers to increase E6AP activity is encompassed by the methods of the disclosure.

Accordingly, It has been found, for example in the case of E6AP that the ability of the enzyme to catalyze the formation of polyubiquitin is dependent on the successful formation of a trimeric structure composed of three identical polypeptides encoded by the UBE3 gene. It has further been found that the activity of E6AP ligase can be modulated to either increase or decrease catalytic activity by interacting the subunits or the trimer with small non-competitive molecules (that prevent trimerization and hence decrease activity) or by promoting the association of the monomers to the trimeric form to increase catalytic activity.

The E6AP ligase protein was initially identified by its interaction with the E6 viral protein encoded by human papilloma virus 16 (HPV16) (Scheffner et al., (1993) Cell 75: 495-505; Huibregtse et al., (1991) EMBO J. 10: 4129-4135; Beer-Romero et al., (1997) Oncogene 14: 595-602). Although p53 degradation is normally mediated by the Mdm2 ubiquitin ligase (Haupt et al., (1997) Nature 387: 296-299), E6 protein is proposed to bind to E6AP ligase and redirect its specificity to p53 (Beer-Romero et al., (1997) Oncogene 14: 595-602; Talis et al., (1998) J. Biol. Chem. 273: 6439-6445). Enhanced degradation of p53 in epithelial cells by the HPV16 and HPV-18 viral strains induces cell transformation and development of cervical and oral cancers, depending on the site of infection (Beaudenon & Huibregtse (2008) BMC Biochem. 9: S4; Lawson et al., (2009) Br. J. Cancer 101, 1351-1356; Muench et al., (2010) Cancer Res. 70: 6913-6924). Similarly, hepatitis C virus encodes the NS5B protein that binds E6AP ligase and induces degradation of the retinoblastoma protein tumor suppressor, increasing the risk of liver cirrhosis and hepatocellular carcinoma (Munakata et al., (2007) PLoS Pathog. 3: 1335-1347; Shirakura et al., (2007) J. Virol. 81: 1174-1185). The E6AP ligase sequence contains a leucine-rich motif (LXXLL) in the N-terminal region to which the E6 viral protein binds (Chen et al., (1998) J. Biol. Chem. 273: 13537-13544; Elston et al., (1998) J. Gen. Virol. 79: 371-374; Be et al., (2001) Biochemistry 40: 1293-1299). Biophysical and structural analyses of the E6-E6AP ligase interaction show that the N-terminal E6 $Zn^{2+}$-binding domain primarily interacts with E6AP, whereas the C-terminal $Zn^{2+}$-binding domain interacts with p53 (Liu et al., (2009) J. Mol. Biol. 386: 1123-1137; Zanier et al., (2005) J. Mol. Biol. 349: 401-412; Zanier et al., (2010) J. Mol. Biol. 396: 90-104; Zanier et al., (2013) Science 339: 694-698; Nominé et al., (2003) Biochemistry 42: 4909-4917). Although the interaction of E6 with E6AP ligase is necessary for degradation of p53, the effect of such interaction on the catalytic activity of E6AP ligase has not been adequately addressed; Kao et al. ((2000) J. Virol. 74: 6408-6417) have shown that ectopic E6 expression increases E6AP ligase autoubiquitination and intracellular turnover.

Full-length E6AP ligase is a protein of 100 kDa; however, only the structure of the truncated E6AP ligase Hect domain in association with its cognate UbcH7 ubiquitin carrier protein has been reported (Huang et al., (1999) Science 286: 1321-1326). The Hect domain architecture displays an L-shape with distinct N-terminal and C-terminal subdomains connected by a flexible hinge region (Huang et al., (1999) Science 286: 1321-1326). The N-terminal subdomain can be further divided into large and small N-terminal subdomains also connected by flexible hinge segments (Huang et al., (1999) Science 286: 1321-1326). The active site $Cys^{820}$ to which ubiquitin forms a thioester intermediate is contained in the C-terminal subdomain (Huang et al., (1999) Science 286: 1321-1326; Scheffner et al., (1994) Proc. Natl. Acad. Sci. U.S.A. 91: 8797-8801). The UbcH7 carrier protein binds to a pocket in the small N-terminal subdomain, but the geometry of the bound UbcH7~ubiquitin thioester relative to $Cys^{820}$ has been a challenge to understanding within the context of a coherent mechanism for $Cys^{820}$~ubiquitin thioester formation and subsequent polyubiquitin chain formation, discussed recently (Ronchi et al., (2013) J. Biol. Chem. 88: 10349-10360). However, kinetic analysis of $^{125}$I-polyubiquitin chain assembly now demonstrates for the first time the presence of two functionally distinct E2~ubiquitin binding sites on the E6AP ligase Hect domain, providing a mechanistically tractable resolution to the problem of active site thioester formation (Ronchi et al., (2013) J. Biol. Chem. 88: 10349-10360). Other kinetic evidence indicates that the canonical UbcH7 binding site presented in the original crystal structure (Huang et al., (1999) Science 286: 1321-1326) functions in chain elongation from the ubiquitin thioester formed at $Cys^{820}$ (Ronchi et al., (2013) J. Biol. Chem. 88: 10349-10360).

Employing $^{125}$I-polyubiquitin chain formation as a functional readout of ligase activity, biochemical and biophysical evidence demonstrates that catalytically active E6-associated protein (E6AP)/UBE3A is an oligomer. Based on an extant structure previously discounted as an artifact of crystal packing forces, we propose that the fully active form of E6AP ligase is a trimer, analysis of which reveals a buried surface of 7508 Å$^2$ and radially symmetric interacting residues that are conserved within the Hect (homologous to E6AP ligase C terminus) ligase superfamily. An absolutely conserved interaction between $Phe^{727}$ and a hydrophobic pocket present on the adjacent subunit is critical for trimer stabilization because mutation disrupts the oligomer and decreases $k_{cat}$ 62-fold but fails to affect E2~ubiquitin binding or subsequent formation of the Hect domain $Cys^{820}$~ubiquitin thioester catalytic intermediate.

Exogenous N-acetyl-L-phenylalanylamide reversibly antagonizes $Phe^{727}$-dependent trimer formation and catalytic activity ($K_i$=12 mM), as does a conserved α-helical peptide corresponding to residues 474-490 of E6AP ligase isoform 1 ($K_i$=22 µM) reported to bind the hydrophobic pocket of other Hect ligases, presumably blocking $Phe^{727}$ intercalation and trimer formation. Conversely, oncogenic human papillomavirus-16/18 E6 protein significantly enhances E6AP ligase catalytic activity by promoting trimer formation ($K_{activation}$=1.5 nM) through the ability of E6 to form homodimers. Recombinant E6 protein additionally rescues the $k_{cat}$ defect of the $Phe^{727}$ mutation and that of a specific loss-of-function Angelman syndrome mutation that promotes trimer destabilization. The present findings codify otherwise disparate observations regarding the mechanism of E6AP ligase and related Hect ligases in addition to suggesting therapeutic approaches for modulating ligase activity.

Homo- and hetero-oligomerization regulate many complex biochemical processes in the cell (Marianayagam et al., (2004) Trends Biochem. Sci. 29: 618-625). Such protein interactions are critical for the mechanism(s) of assembling polyubiquitin signals during key events of cell regulation (Heer et al., (2011) *Biochemistry* 50, 1376-1383; Spitkovsky et al., (1996) *Oncogene* 13: 1027-1035; Streich et al., (2013) *J. Biol. Chem.* 288: 8209-8221; Kiyono et al., (1998) *Nature* 396: 84-88; Kentsis et al., (2002) *Proc. Natl. Acad. Sci. U.S.A.* 99: 15404-15409; Sun et al., (2004) *Mol. Cell* 14: 289-301). Assembly of $^{125}$I-polyubiquitin chains by GST-E6AP ligase is reduced when the affinity tag is removed following digestion with thrombin. Experiments herein disclosed indicated that the ability of GST to dimerize promotes oligomerization of E6AP, confirmed by the quantitative inhibition of ligase-catalyzed chain formation by free GST, GST-E6APΔ495, and GST-E6APC820A, as shown in FIGS. 2A-2F.

The ability of thrombin-processed E6APΔ495 and E6APC820A to similarly inhibit wild-type GST-E6AP ligase polyubiquitin chain formation demonstrates that oligomerization is an intrinsic property of the Hect ligase, with the interaction interfaces probably spanning the N-terminal targeting and C-terminal Hect domains of the ligase (FIGS. 2A-2E). In addition, co-purification of recombinant baculoviral-expressed His$_6$-E6AP ligase with full-length E6AP ligase lacking the His$_6$ affinity tag is consistent with oligomerization of the ligase (FIG. 3B). The progressive increase in kcat for E6AP-catalyzed $^{125}$I-polyubiquitin chain assembly with the absence of competing degradative fragments is consistent with a role for oligomerization in the activity of E6AP ligase (Table 1).

TABLE 1

Effect of E6AP ligase length on chain formation kinetics

| | $K_m$ (nM) | $k_{cat}$ (s$^{-1}$) | $k_{cat}/K_m$ (M$^{-1}$ s$^{-1}$) |
|---|---|---|---|
| Heterogeneous GST-E6AP | 58 ± 6 | 3.1 ± 0.9 × 10$^{-2}$ | 5.4 × 10$^5$ |
| E6AP ligase Hect domain | 91 ± 25 | 7.0 ± 0.1 × 10$^{-4}$ | 8.5 × 10$^3$ |
| GST-E6AP ligase Hect domain | 89 ± 11 | 3.2 ± 0.1 × 10$^{-4}$ | 3.6 × 10$^3$ |
| Homogeneous His$_6$-E6AP | 46 ± 7 | 6.3 ± 0.3 × 10$^{-1}$ | 1.3 × 10$^7$ |

Figure 4A:
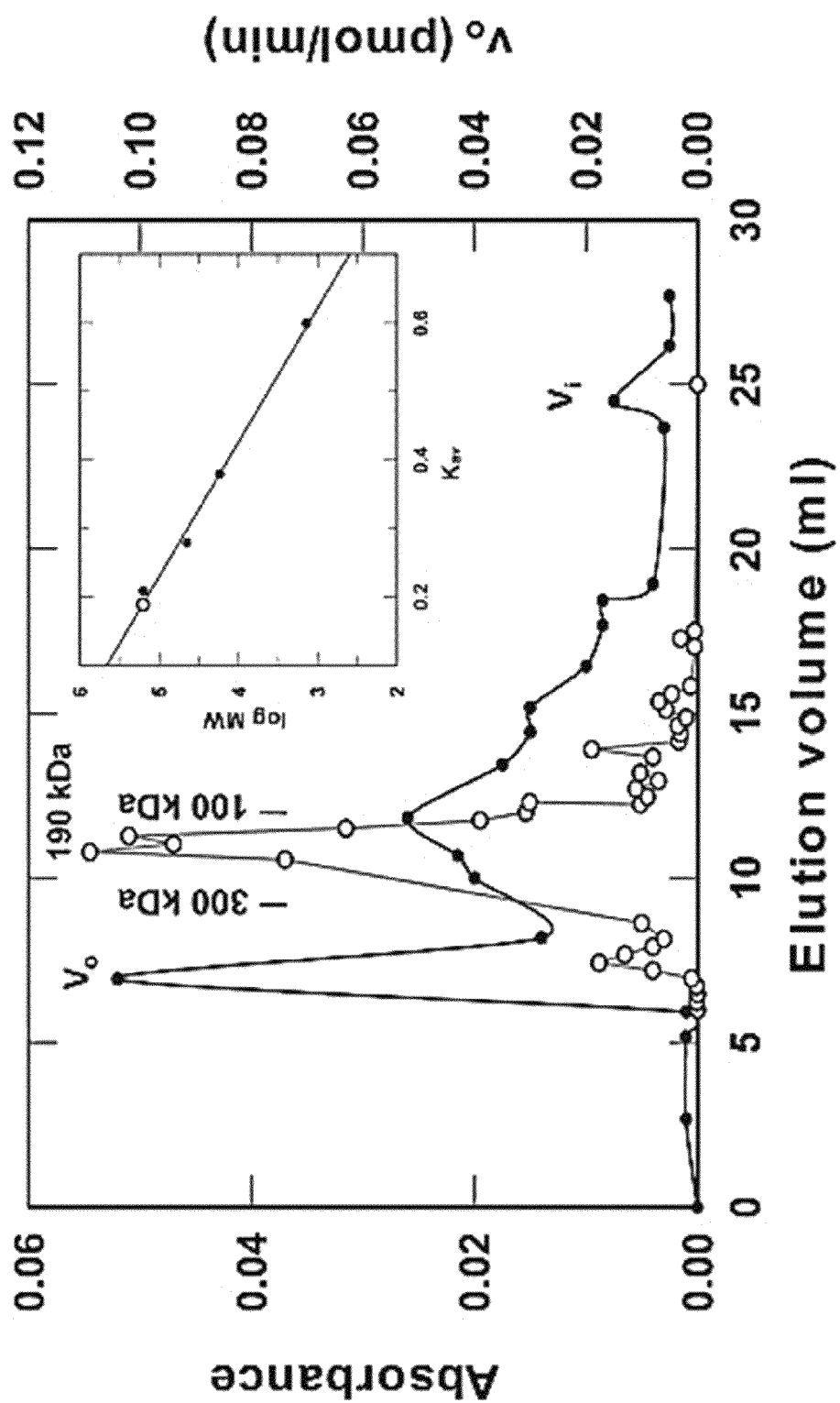
FIGS. 4A-4C illustrate that functional E6AP ligase is an oligomer.
Figure 4B:
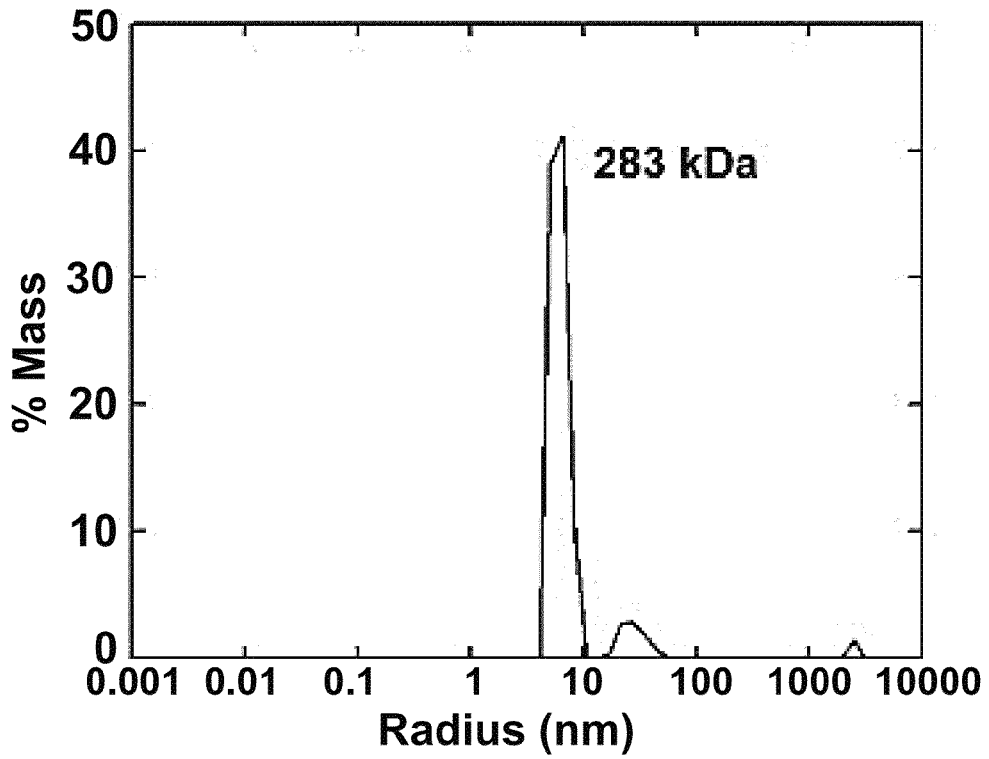
Figure 4C:
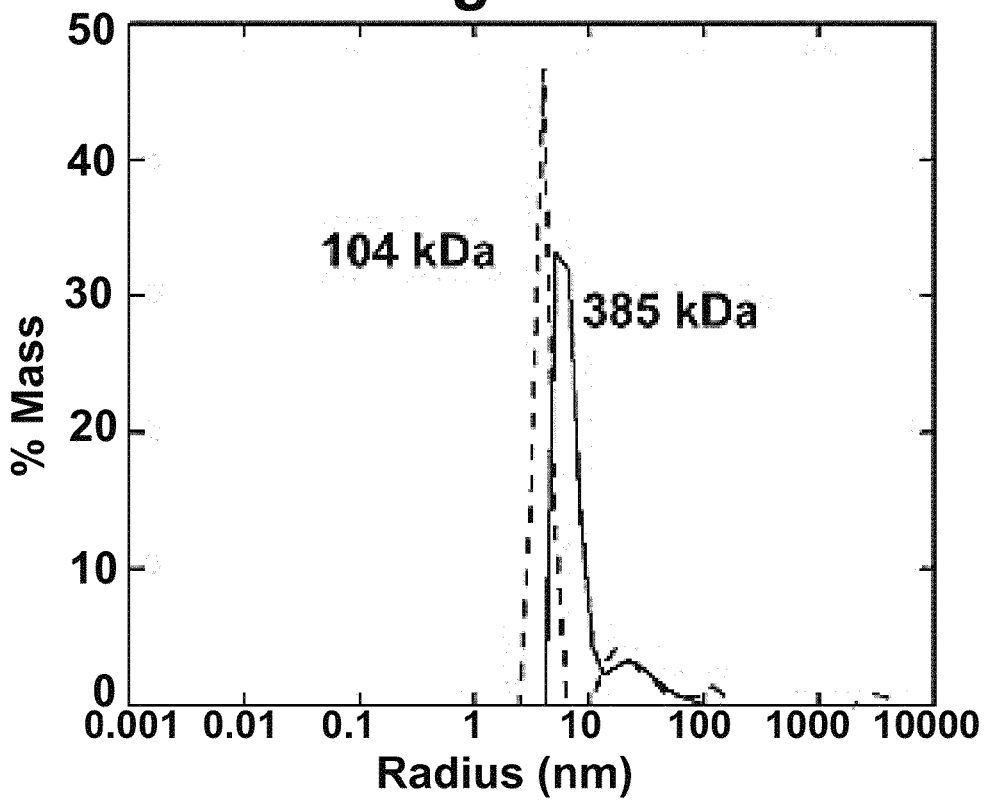

Finally, static light-scattering measurements are consistent with the homotrimer as the catalytically relevant form of E6AP ligase (FIGS. 4B and 4C).

It has now been shown that a paralogous F727D mutation intended to more completely disrupt trimer formation significantly reduces the ability of the enzyme to catalyze elongation of polyubiquitin chains to a level less than 2% of the wild-type enzyme (Table 2), concomitant with dissociation of the oligomer (FIGS. 4A-4C).

TABLE 2

Summary of kinetic constants

| | $K_m$ (nM) | $k_{cat}$ (s$^{-1}$) | $k_{cat}/K_m$ (M$^{-1}$ s$^{-1}$) |
|---|---|---|---|
| GST-E6AP-UbcH7a | 58 ± 8 | 3.1 ± 0.9 × 10$^{-2}$ | 5.4 × 10$^5$ |
| GST-E6APF727D-UbcH7b | 72 ± 25 | 5.0 ± 0.7 × 10$^{-4}$ | 7.6 × 10$^3$ |
| GST-E6APY533A-UbcH7 | 40 ± 12 | 3.1 ± 0.2 × 10$^{-3}$ | 7.9 × 10$^4$ |
| GST-E6APD543A-UbcH7b | 540 ± 400 | 4.0 ± 1.0 × 10$^{-3}$ | 7.5 × 10$^3$ |
| GST-E6APR626A-UbcH7b | 150 ± 50 | 2.0 ± 0.2 × 10$^{-4}$ | 1.3 × 10$^3$ |
| GST-E6APK688A-UbcH7 | 39 ± 10 | 5.2 ± 0.4 × 10$^{-2}$ | 1.3 × 10$^5$ |

As noted previously for the F727A mutant (Wang et al., (2007) *J. Cell Biol.* 177: 613-624), mutation of Phe$^{727}$ to aspartic acid has no effect on formation of the essential Cys$^{820}$~ubiquitin thioester intermediate.

In silico PISA analysis of the subunit interfaces present within the E6AP ligase trimer identifies a cohort of conserved residues within the 7508 Å$^2$ buried by oligomerization. Of the significant number of hydrogen bond and salt bridge interactions identified by PISA, the conserved radially symmetric network of interactions represented by the intersubunit intercalation of Phe$^{727}$ into the hydrophobic pocket present on the adjacent subunit appears important because mutation of Phe$^{727}$ or antagonizing the interaction by the addition of Ac-PheNH$_2$ disrupts trimer formation and significantly reduces activity. The linearity of the double reciprocal plots in the presence of Ac-PheNH$_2$ (FIGS. 5A and 5B) and the agreement between the empirical K of 12 mM and the value of 27 mM predicted from the calculated binding energy of Phe$^{727}$ (−2.13 kcal/mol) are consistent with the amino acid derivative binding at the unique hydrophobic pocket present in the subunit interface.

Figure 6A:
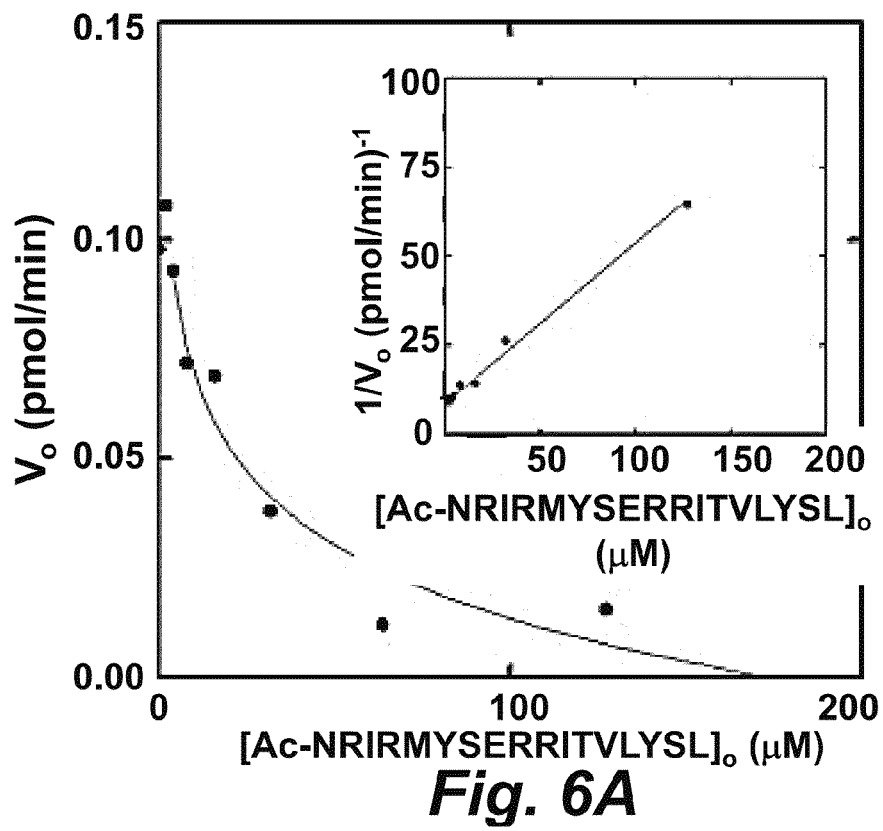
FIGS. 6A-6C illustrate that the N-terminal α-helical peptide inhibits E6AP ligase function.
Figure 6B:
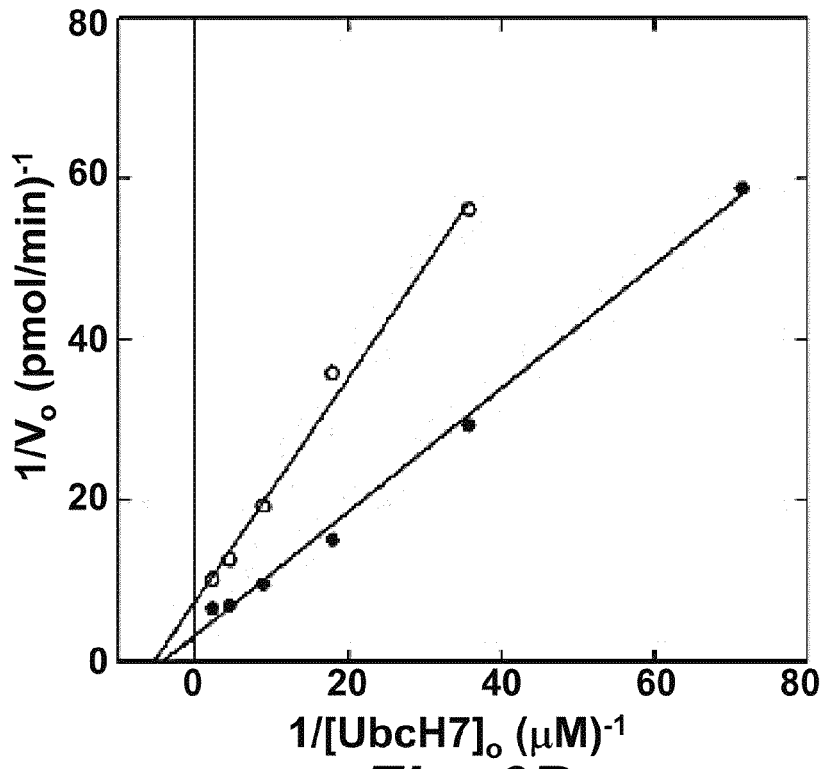
Figure 6C:
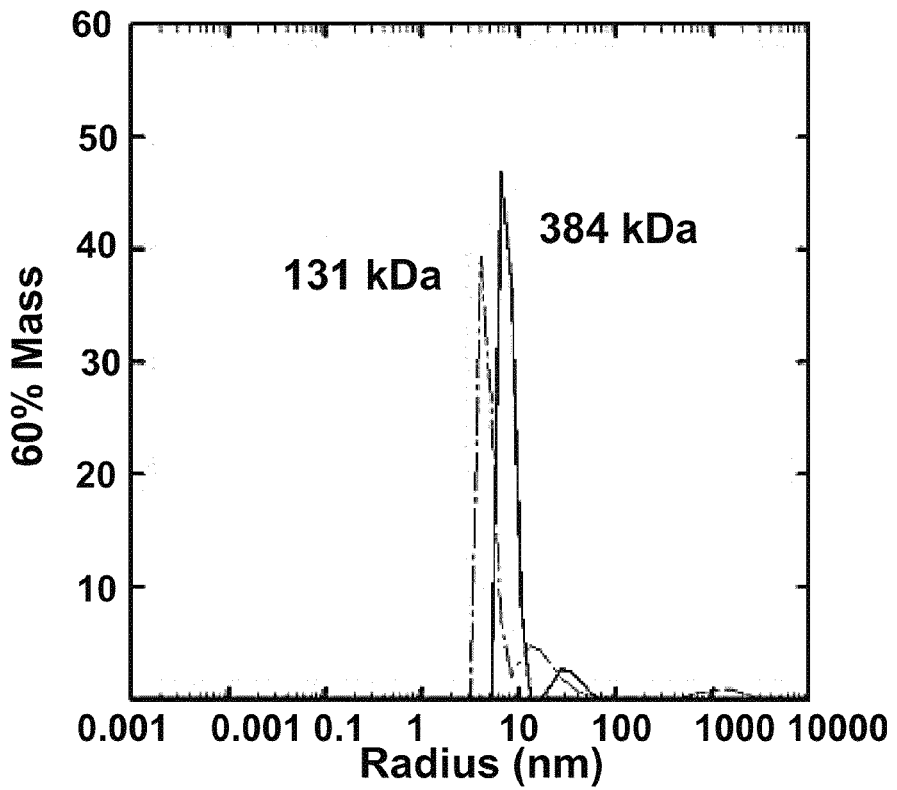

It has now been shown that E6AP ligase is unique in forming a trimer. The 1 DF5 E6AP ligase trimer is also notable in being the only Hect domain structure lacking an additional N-terminal sequence segment present in other paralogs. In these other structures, a conserved α-helix within this sequence binds to the hydrophobic pocket otherwise occupied by Phe$^{727}$ in the E6AP ligase trimer (Verdecia et al., (2003) *Mol. Cell* 11: 249-259; Ogunjimi et al., (2010) *J. Biol. Chem.* 285: 6308-6315; Pandya et al., (2010) *J. Biol. Chem.* 285: 5664-5673; Maspero et al., (2011) *EMBO Rep.* 12: 342-349; Kamadurai et al., (2009) *Mol. Cell* 36: 1095-1102). It has now been shown that E6AP ligase residues 474-490 (SEQ ID NO: 1), corresponding to the α-helical region, act as a non-competitive inhibitor of $^{125}$I-polyubiquitin chain formation with an affinity (K$_i$=22±2 μM) considerably greater than that of Ac-PheNH$_2$ (K$_i$=12±3 mm), as shown in FIGS. 6A-6C. The presence of the additional α-helical segment is reported to enhance the intrinsic stability of the Hect domain and to reduce autoubiquitination (Pandya et al., (2010) *J. Biol. Chem.* 285: 5664-5673, 74). The latter has been interpreted as demonstrating a regulatory role for the interaction between the α-helical segment and the hydrophobic pocket in the native full-length structure.

A second subunit interface identified as important for trimer activity localizes to interactions among Tyr$^{533}$ and Asp$^{543}$ within the large N-terminal subdomain, and the small N-terminal subdomain residue Arg$^{626}$ (Chan et al., (2013) *Biochemistry* 52: 3119-3129) of the adjacent subunit, as shown in FIGS. 7A-7E. These residues form a network of hydrogen-bonded interactions that appear to stabilize the trimer because individual mutation of each significantly affects $k_{cat}$ but with little consequence for UbcH7~ubiquitin thioester binding (Table 2).

The functional effects of these mutations collectively support the trimer as the catalytically relevant structure for E6AP. Mutation of Asp$^{543}$ appears to be the single exception because its mutation affects both $k_{cat}$ and binding of the UbcH7~ubiquitin thioester substrate (Table 2). The latter may reflect a structural contribution for the side chain interactions of Asp$^{543}$ or the special role for the residue in bridging the effects of Tyr$^{533}$ and Arg$^{626}$ (FIGS. 7A-7E), which makes its mutation equivalent to a double mutant. In contrast, disrupting the hydrogen bond between Lys$^{688}$ in the small N-terminal subdomain and Glu$^{535}$ in the adjacent large N-terminal subdomain by mutation of the former has no consequence, indicating that the effects of the previous mutations are specific to those residues rather than a general feature of the interface. This subunit interface harbors Tyr$^{636}$, which Chan et al. (Chan et al., (2013) *Biochemistry* 52: 3119-3129) have identified as a substrate for c-Abl phosphorylation in the regulation of E6AP ligase function. It was speculated (Chan et al., (2013) *Biochemistry* 52: 3119-3129) that the inhibition of E6AP ligase activity observed on phosphorylation of Tyr$^{636}$ might result from blocking oligomerization of the enzyme. The observations of the disclosure and the effect of mutation on other residues within this region support a role for Tyr$^{636}$ in regulating trimer formation and E6AP ligase activity.

The ability of E6 protein to recruit p53 to E6AP ligase for targeted degradation is the accepted paradigm by which HPV-16 transforms infected epithelial cells (Huibregtse et al., (1991) *EMBO J.* 10: 4129-4135; Scheffner et al., (1990) *Cell* 63: 1129-1136; Huibregtse et al., (1993) *Mol. Cell Biol.* 13: 4918-4927). Structural studies demonstrating dimerization of E6 protein have more recently accounted for the observed stoichiometry of the resulting E62-p534 complex (Zanier et al., (2010) *J. Mol. Biol.* 396: 90-104; Medcalf & Milner (1993) *Oncogene* 8: 2847-2851).

Given the observation herein disclosed that oligomeric E6AP ligase is the catalytically competent form of the ligase, the ability of E6 protein to dimerize and thereby promote E6AP-catalyzed polyubiquitin chain formation was examined. The data of FIGS. 8A-8C demonstrate that E6 protein is a potent non-essential activator of E6AP ligase catalytic activity within a low nanomolar concentration range ($K_{activation}$=1.5 nM). The $K_{activation}$ for ligase stimulation, representing the binding of E6 to E6AP, is significantly lower than the 4 μM $K_d$ for binding of the viral protein to E6AP ligase reported previously by surface plasmon resonance (Zanier et al., (2005) *J. Mol. Biol.* 349: 401-412), reflecting the enhanced entropically coupled affinity associated with binding to linked sites (Page & Jencks (1971) *Proc. Natl. Acad. Sci. U.S.A.* 68: 1678-1683).

Figure 8A:
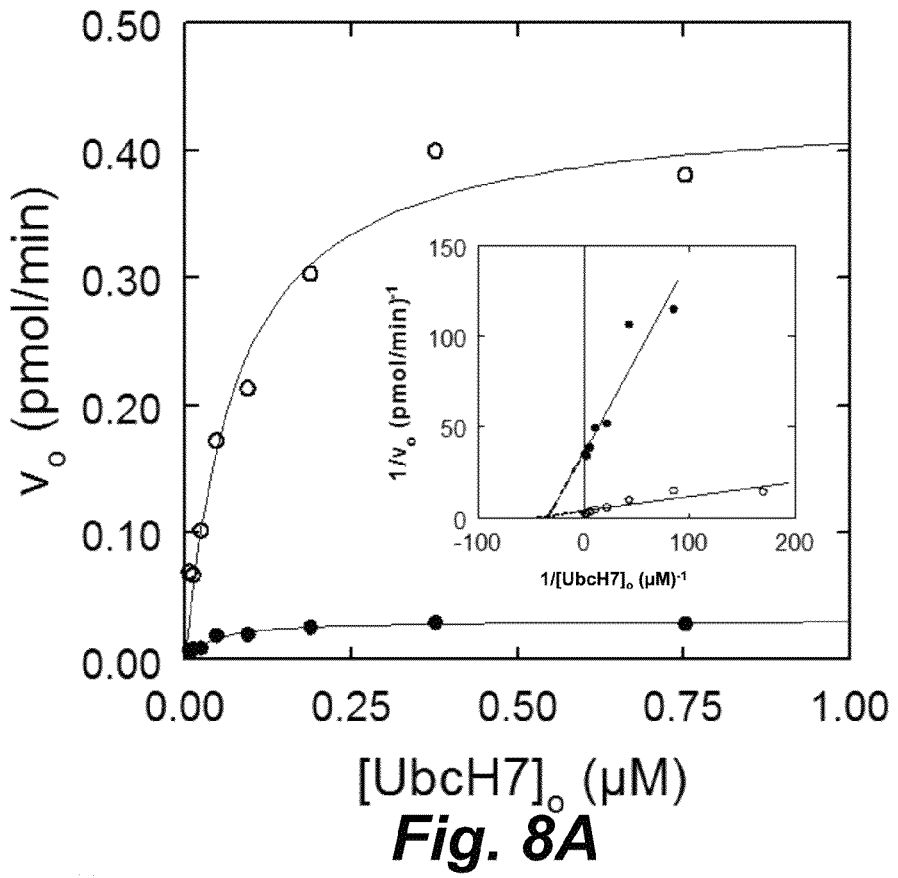
FIGS. 8A-8D illustrate that E6 protein enhances E6AP ligase activity and rescues selected Angelman syndrome mutations.

The latter indicates that E6 protein probably functions at intracellular concentrations significantly lower than suggested by the isolated in vitro equilibrium binding affinity. In the absence of substrate, E6AP ligase catalyzes the assembly of free and anchored polyubiquitin chains, the latter attached to the ligase through autoubiquitination (Ronchi et al., (2013) *J. Biol. Chem.* 288, 10349-10360). This bifurcation of products is proposed to occur by partitioning of a Cys$^{820}$~polyubiquitin intermediate between transfer to water or a lysine present on the ligase, respectively (Ronchi et al., (2013) *J. Biol. Chem.* 288, 10349-10360). The addition of E6 protein uniformly enhances the formation of both $^{125}$I-polyubiquitin products, consistent with the partitioning model (FIG. 8C). These observations anticipate that E6 protein-dependent epithelial cell transformation may arise in part through a general stimulation of ligase activity toward its normal cohort of endogenous targets rather than serving exclusively as a binding adapter to target a small subset of alternate targets, such as p53 (FIG. 8A). Such a proposal is consistent with earlier observations that an E6 SAT8-10 mutant defective in targeting E6AP-dependent p53 degradation (Kao et al., (2000) *J. Virol.* 74: 6408-6417) but retaining the ability to immortalize human epithelial cells, induce colony growth on soft agar, and stimulate telomerase activity (Spitkovsky et al., (1996) *Oncogene* 13: 1027-1035; Kiyono et al., (1998) *Nature* 396: 84-88) also simulates E6AP ligase autoubiquitination and degradation in vitro (Kao et al., (2000) *J. Virol.* 74: 6408-6417).

The 14-fold stimulation in E6AP ligase activity at saturating E6 protein suggests that only 0.7% of the active ligase, determined by stoichiometric Cys$^{820}$~$^{125}$I-ubiquitin thioester formation, is present as the active trimer under the conditions of FIG. 8A, although it cannot be ruled out that an intermediate level of activity from potential dimeric species derived from the trimeric structure. Consistent with the remarkable effect of E6 in promoting oligomerization, the viral protein complements the kinetic phenotypes resulting from the F727D, R626A, and Y533A mutations, the latter being a documented Angelman syndrome mutation site (Fang et al., (1999) *Hum. Mol. Genet.* 8: 129-135). Because the F727D mutation results in defective trimer formation, functional complementation of the R626A and Y533A mutations suggests that they as well represent trimer formation defects.

Identification of oligomeric E6AP ligase as the trimer or multiples thereof, as the catalytically relevant form of the ligase explains a number of previous observations in the literature and provides potential pharmacological approaches to modulate activity of the enzyme. Accordingly, Ac-PheNH$_2$ provides an embodiment of an E6AP ligase antagonists targeted to the disruption of oligomerization. Similarly, E6 protein provides an example of an embodiment of an agent that can modulate E6AP ligase oligomerization (i.e. increase multimerization) that could serve as additional therapeutic targets.

The intrinsic ability of E6AP ligase to form free polyubiquitin chains in the absence of substrate was used as a reporter activity related to the catalytic behavior of the enzyme. Kinetic analysis of free chain formation in biochemically-defined assays defined the E3 specificity of E6AP. Functional studies demonstrate that polyubiquitin chain formation requires multimerization of the E6AP ligase, and most especially trimer formation to generate a degradation signal. The present disclosure, therefore, encompasses novel methods of modulating E6AP ligase catalytic activities, compounds to effectuate the dissociation of an E6AP ligase trimer required for E6AP ligase to form a polyubiquitin degradation signal, and therapeutic applications relating to E6AP ligase catalytic activities.

One aspect of the disclosure encompasses embodiments of a method of modulating the activity of a ubiquitin-protein E3 ligase comprising contacting a ubiquitin-protein E3 ligase with an agent that reduces ligase oligomer formation or with an agent that increases ligase oligomer formation.

In some embodiments of this aspect of the disclosure, the oligomer can be a homooligomer of at least two ubiquitin-protein E3 ligase polypeptides.

In some embodiments of this aspect of the disclosure, the ubiquitin-protein E3 ligase can be E6AP encoded by the UBE3A gene.

In some embodiments of this aspect of the disclosure, the agent that reduces ubiquitin-protein E3 ligase oligomer formation can be a non-competitive inhibitor of ligase activity.

In some embodiments of this aspect of the disclosure, the agent is N-acetyl-L-phenylalanylamide.

In some embodiments of this aspect of the disclosure, the agent that increases ubiquitin-protein E3 ligase oligomer formation can be a peptide fragment.

In some embodiments of this aspect of the disclosure, the agent that increases ubiquitin-protein E3 ligase oligomer formation can be a peptide fragment from a human papilloma virus.

In some embodiments of this aspect of the disclosure, the agent that increases ubiquitin-protein E3 ligase oligomer formation can be an E6 polypeptide, or a peptide fragment therefrom, of a human papilloma virus.

In some embodiments of this aspect of the disclosure, the E6AP can comprise a mutated amino acid residue or residues that result in a pathological condition in a human or animal subject.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Materials and Methods: Bovine ubiquitin and creatine phosphokinase were purchased from Sigma. Ubiquitin was further purified to apparent homogeneity by FPLC and quantitated spectrophotometrically (Baboshina & Haas (1996) *J. Biol. Chem.* 271, 2823-2831). Ubiquitin was radioiodinated by the Chloramine-T procedure to yield a specific radioactivity of approximately 15,000 cpm/pmol using carrier-free $Na^{125}I$ according to Haas A. L. ((2005) Methods Mol. Biol. 301: 23-35). Human erythrocyte Uba1 (UBA1) was purified to apparent homogeneity from outdated human blood (Haas A. L. (2005) Methods Mol. Biol. 301: 23-35). Active Uba1 was quantitated by the stoichiometric formation of $^{125}I$-ubiquitin thioester (Haas A. L. (2005) *Methods Mol. Biol.* 301: 23-35; Haas & Rose (1982) *J. Biol. Chem.* 257: 10329-10337; Haas & Bright (1988) *J. Biol. Chem.* 263: 13258-13267). Human recombinant UbcH7 (UBE2L3) was that described previously (Tokgöz et al., (2012) *J. Biol. Chem.* 287: 311-321; Ronchi & Haas (2012) *Methods Mol. Biol.* 832: 197-218), and active E2 concentration was quantitated by the Uba1-dependent stoichiometric formation of UbcH7~$^{125}I$-ubiquitin thioester (Ronchi et al., (2013) *J. Biol. Chem.* 288, 10349-10360; Siepmann et al., (2003) *J. Biol. Chem.* 278: 9448-9457). The E2 protein was stored at −80° C. in small aliquots and was stable for more than 6 months although subject to activity loss with successive freeze-thaw cycles (Siepmann et al., (2003) *J. Biol. Chem.* 278: 9448-9457). The N-acetyl-L-phenylalanylamide (Ac-PheNH$_2$; E-1160) was obtained from Bachem Americas. The N-acetyl-NRIRMYSERRITVLYSL peptide (SEQ ID NO: 1) (purity >95%) was obtained from PEPTIDE 2.0 Inc. All references are incorporated herein in their entireties.

Example 2

Generation and Purification of Recombinant E6AP: Human E6AP ligase isoform 3 (UBE3A; IMAGE clone NM00046.2) was subcloned into pGEX4T1 to yield pGEX4T1-E6AP ligase as described previously (Ronchi et al., (2013) *J. Biol. Chem.* 288, 10349-10360). The sequence for E6AP ligase isoform 3 differs from isoform 1, from which the original crystal structure was determined (Huang et al., (1999) *Science* 286: 1321-1326), by the presence of an additional 20 amino acids at the N terminus. To facilitate comparison with the crystal structure, residues for isoform 3 are referenced to the paralogous position of isoform 1 (i.e. by subtracting 20 from the isoform 3 residue number. Thus, the E6APF727D, E6APY533A, E6APD543A, E6APR626A, and E6APK688A mutants were generated from pGEX4T1-E6AP ligase using the QuikChange protocol of Stratagene to yield pGEX4T1-E6APF727D, pGEX4T1-E6APY533A, pGEX4T1-E6APD543A, pGEX4T1-E6APR626A, and pGEX4T1-E6APK688A, respectively.

The E6APΔ495 truncation lacking the C-terminal Hect domain was generated by inserting a STOP codon after codon 495 of pGEX4T1-E6AP ligase to yield pGEX4T1-E6APΔ495. Residues 450-852 of full-length E6AP ligase were subcloned by PCR into the BamHI/NotI sites of pGEX4T1 to yield pGEX4T1-E6AP-Hect, from which was expressed the GST-E6AP-Hect domain fusion protein. The active site $Cys^{820}$ was similarly mutated to alanine by the QuikChange protocol to yield GST-E6AP-HectC820A protein. The coding regions for all E6AP ligase clones were sequenced to preclude cloning artifacts and to verify the desired mutation.

Wild type and mutant GST-E6AP ligase proteins were expressed and purified as described previously (Ronchi et al., (2013) *J. Biol. Chem.* 288, 10349-10360; Ronchi & Haas (2012) *Methods Mol. Biol.* 832: 197-218, incorporated herein by reference in their entireties). The activities of GST-E6AP ligase and its mutants were quantitated by their stoichiometric formation of $^{125}I$-ubiquitin thioester (Ronchi et al., (2013) *J. Biol. Chem.* 288, 10349-10360; Ronchi & Haas (2012) *Methods Mol. Biol.* 832: 197-218; van Woerden et al., (2007) *Nat. Neurosci.* 10: 280-282). Unless otherwise noted, the GST moiety was not processed from the fusion proteins by thrombin digestion (Ronchi et al., (2013) *J. Biol. Chem.* 288, 10349-10360).

The full-length E6AP ligase sequence was subsequently cloned by PCR into the BamHI/HindIII sites of pFastBac Htb (Invitrogen) for baculoviral expression of the corresponding His$_6$-E6AP. After bacmid amplification, the complete insert was sequenced to confirm the absence of cloning errors. The bacmid was transfected into Sf9 insect cells, and then the P1 virus was isolated and amplified as a P2 stock. The P2 stock was then used to transfect Sf9 cells ($3.6 \times 10^7$ cells/T45 flask, $10^5$ virus particles/T45 flask), and protein expression was allowed to proceed for 5 days as recommended by the Bac-to-Bac Baculovirus Expression System manual (Invitrogen). Full-length recombinant His$_6$-E6AP ligase was isolated from the medium by affinity purification using a 1.5×3.0 cm His-Trap HP column (Amersham Biosciences). The column was equilibrated in 50 mM Tris-HCl (pH 8.0) and 20 mM imidazole, and the bound protein was eluted in 50 mM Tris-HCl (pH 8.0) containing 300 mM imidazole. After elution, the protein was equilibrated by dialysis into 50 mM Tris-HCl (pH 7.5) containing 300 mM NaCl and 1 mM DTT. Typically 1.6-2 mg of affinity-purified $His_6$-E6AP ligase protein could be isolated from 13 T150 flasks, of which 10-40% was active by the Uba1-dependent formation of E6AP~$^{125}$I-ubiquitin thioester (Ronchi et al., (2013) *J. Biol. Chem.* 288, 10349-10360; Ronchi & Haas (2012) *Methods Mol. Biol.* 832: 197-218).

Example 3

Expression and Purification of Recombinant HPV16 E6 Protein: HPV16 E6 protein coding sequence (GenBank Accession No. EF122273.1; GI 119710759) was subcloned into BamHI/XhoI sites of pGEX4T3 to yield pGEX4T3-E6 (HPV16). The E6(HPV16)Δ91 recombinant protein was obtained by inserting a STOP codon after codon 91 by the QuikChange protocol of Stratagene to yield pGEX4T3-E6 (HPV16)Δ91. The HPV16 E6 C-terminal domain corresponded to residues 89-158 and was subcloned into BamHI/XhoI sites of pGEXT4T1 by PCR to yield pGEX4T1-E6Ct. *Escherichia coli* BL21 (DE3) cells harboring pGEX-E6 (HPV16), pGEX4T3-E6(HPV16)Δ91, or pGEX4T1-E6 (HPV16)E6Ct were grown at 37° C. and then induced at $A_{600}$ of 0.6 by the addition of isopropyl-1-thio-β-d-galactopyranoside (IPTG) to a final concentration of 0.4 mM. After 3 h at 37° C., cells were harvested by centrifugation at 6000×g for 30 min and then resuspended in 50 mM Tris-HCl (pH 7.5) containing 150 mM NaCl and 1 mM DTT (Siepmann et al., (2003) *J. Biol. Chem.* 278: 9448-9457). Cells were lysed by Emulsiflex (Avestin) and then centrifuged at 30,000×g for 30 min (Siepmann et al., (2003) *J. Biol. Chem.* 278: 9448-9457). Recombinant GST-E6(HPV16) fusion proteins were purified on glutathione-Sepharose, processed with thrombin, and then passed through a second glutathione-Sepharose column to remove free GST (Siepmann et al., (2003) *J. Biol. Chem.* 278: 9448-9457). The total protein content calculated by the theoretical 280 nm extinction coefficient yielded 2.4 mg/liter of culture except for E6(HPV16)Δ91, which yielded 0.5 mg/liter of culture. The proteins were flash frozen in small aliquots and stored at −80° C.

Example 4

E6AP-catalyzed Polyubiquitin Chain Formation Requires Oligomerization: Processing of GST-E6AP ligase fusion protein with thrombin resulted in a consistent 15-30% decrease in activity that resulted from a proportionally lower $k_{cat}$ but without effect on the $K_m$ for UbcH7~$^{125}$I-ubiquitin binding. Because GST protein is known to dimerize, one interpretation posits that GST promotes oligomerization of E6AP ligase that results in the increased $k_{cat}$. Consistent with this model, the addition of free GST to disrupt the putative oligomerization of GST-E6AP ligase showed a biphasic concentration dependence, as shown in FIG. 2A.

Figure 2A:
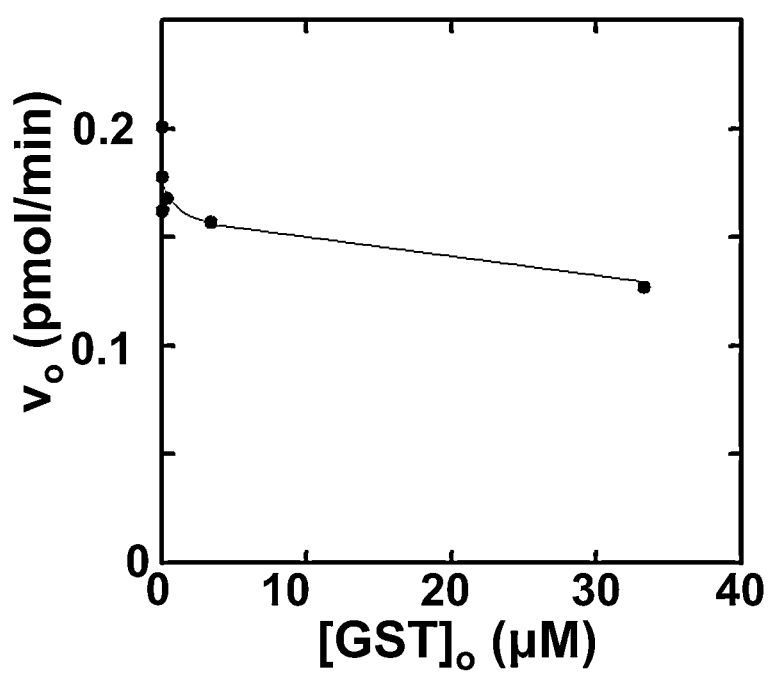
FIGS. 2A-2F illustrates that E6AP ligase-catalyzed polyubiquitin chain-formation requires oligomerization.
Figure 2B:
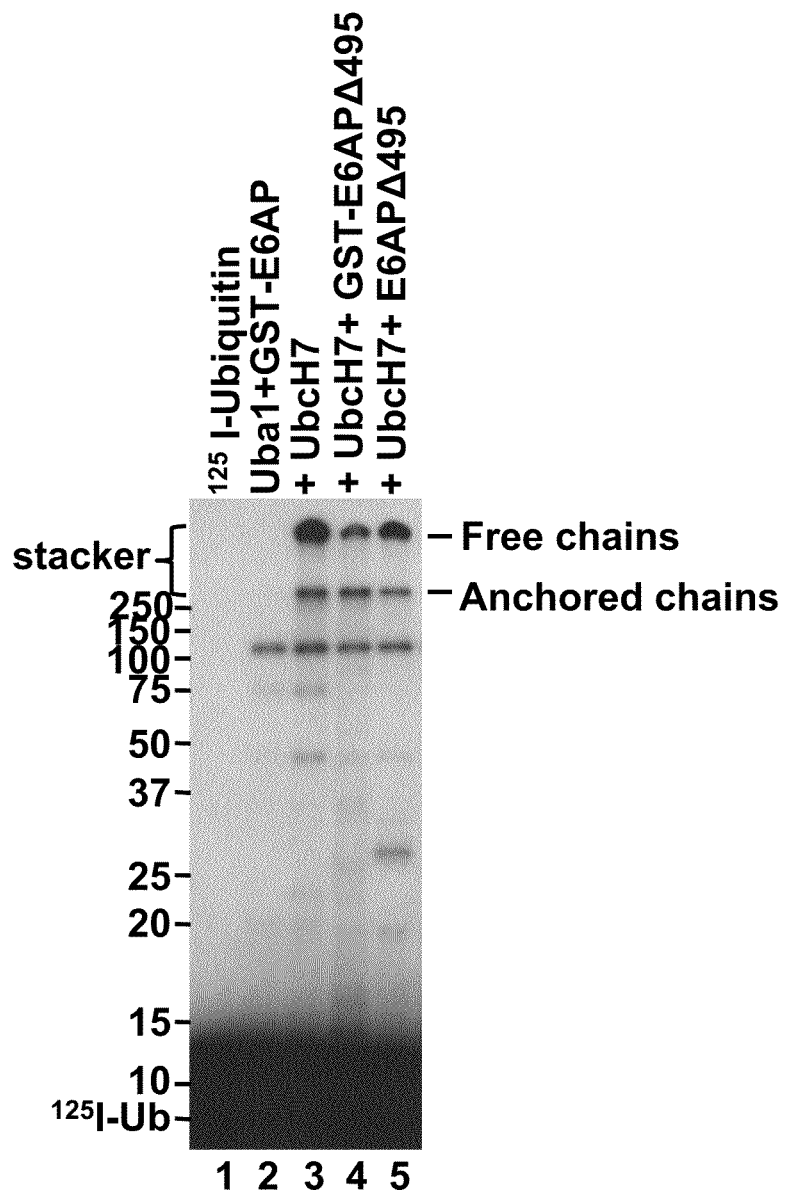

At free GST concentrations less than 5 μM, the abrupt concentration-dependent decrease in the initial rate of polyubiquitin chain formation exhibited a K½ of approximately 1 μm, whereas at higher concentrations, there was a linear reduction in the initial rate with $[GST]_o$ (FIG. 2A). The linear phase at higher GST concentrations coincided with the appearance of a band of monoubiquitinated GST and probably results from competition of this reaction with polyubiquitin chain elongation. In contrast, the decrease in rate occurring at lower GST concentrations was consistent with disruption of GST-E6AP ligase homodimers by free GST because the $K_d$ for GST dimerization is 0.6 μm (Ronchi et al., (2013) *J. Biol. Chem.* 288, 10349-10360).

To directly evaluate the potential contribution of E6AP ligase oligomerization to catalytic activity, a STOP codon was introduced in the GST-E6AP ligase coding region to truncate the Hect domain from E6AP, generating GST-E6APΔ495, to test whether the truncated protein could disrupt oligomerization in a manner similar to the free GST moiety as described in Example 3 above. The addition of either 54 μM GST-E6APΔ495 or 66 μM thrombin-processed E6APΔ495 to wild-type enzyme decreased the initial rate of GST-E6AP-catalyzed polyubiquitin chain formation (FIGS. 2B-2E). When the experiment was repeated at different concentrations of either GST-E6APΔ495 or E6APΔ495, hyperbolic concentration-dependent decreases in the initial rates of polyubiquitin chain formation resulted. At higher concentrations GST-E6APΔ495 and E6APΔ495 quantitatively blocked wild-type GST-E6AP-catalyzed polyubiquitin chain formation.

Nonlinear hyperbolic regression analysis yielded $K_i$ values of 12±3 and 19±8 μM for GST-E6APΔ495 and E6APΔ495, corresponding to $\Delta G_{binding}$ values of −6.7 and −6.4 kcal/mol, respectively. Although the individual $K_i$ values are not statistically different, the corresponding $\Delta\Delta G_{binding}$ for contribution of the GST moiety to GST-E6AP ligase dimerization predicts a $K_d$ for GST association of 1.6 μM, in good agreement with the published value of 0.6 μM (66).

Figure 2C:
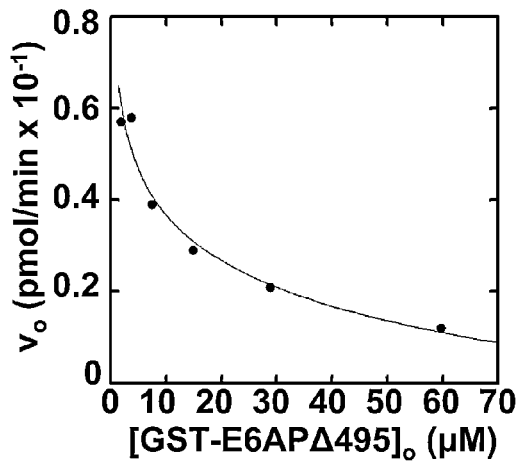
Figure 2D:
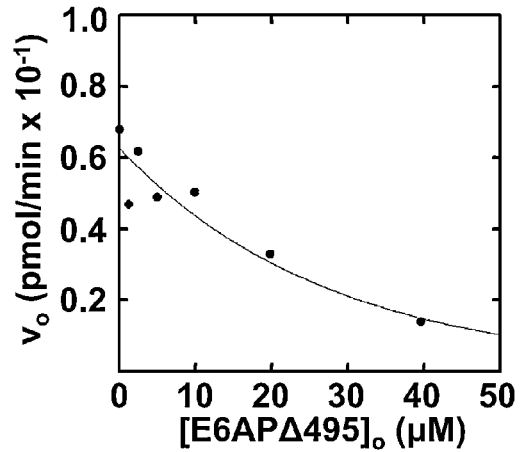
Figure 2E:
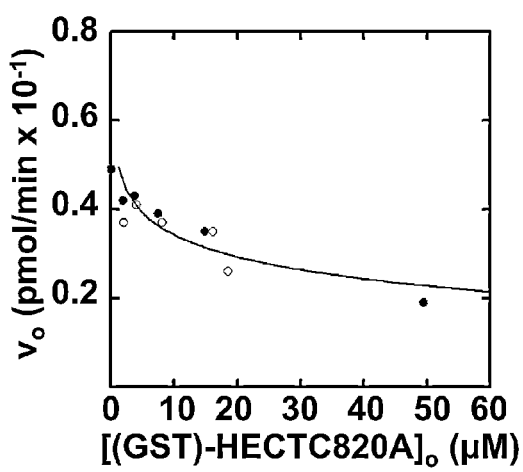
Figure 2F:
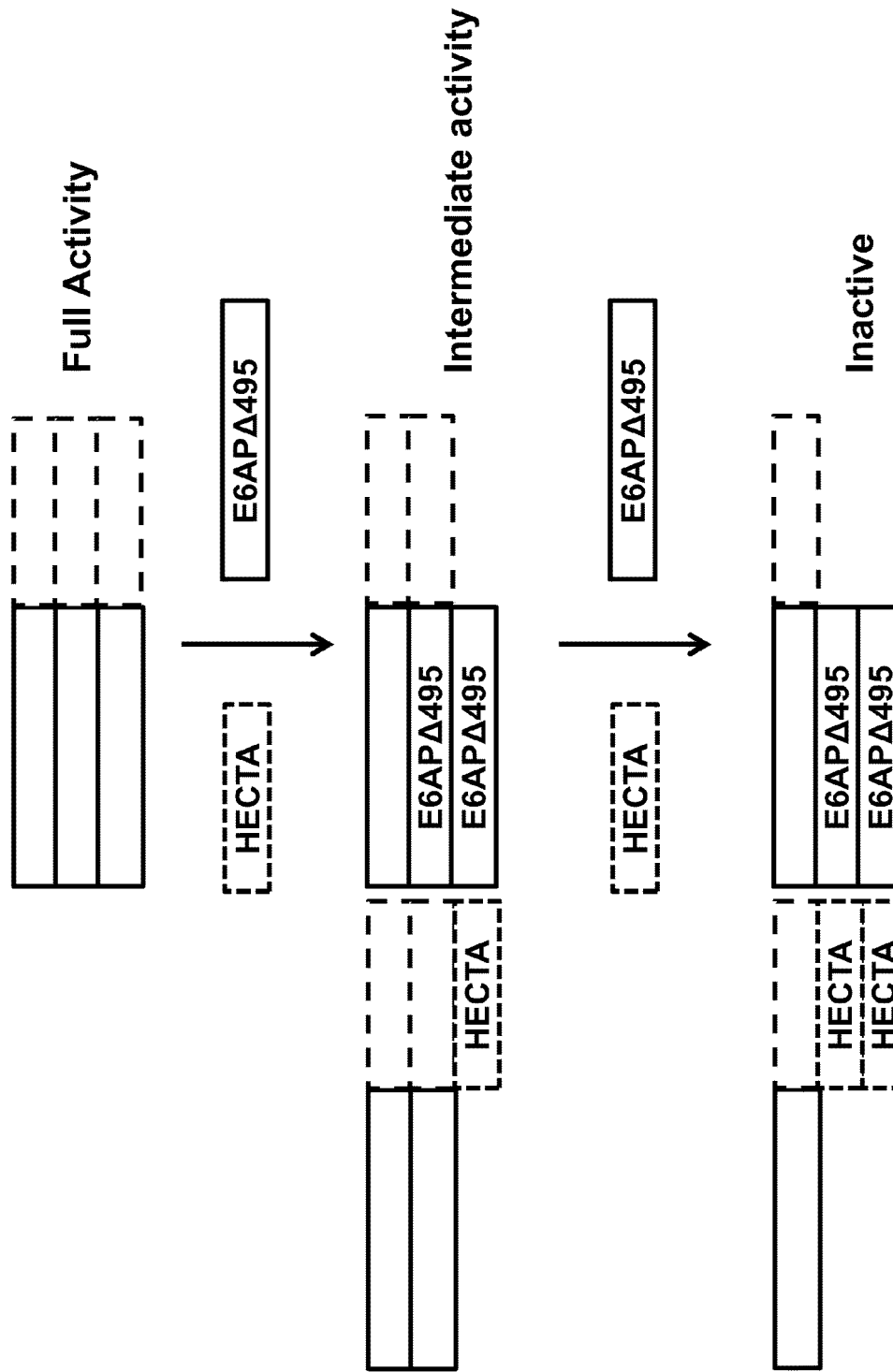

Results identical to those of FIGS. 2C and 2D were obtained when the experiments were repeated with catalytically inactive GST-E6AP-HectC820A or E6AP-HectC820A in which the active site $Cys^{820}$ of the Hect domain was mutated to alanine, yielding $K_i$ values of 31±4 and 27±9 μM, respectively (FIG. 2E). Inhibition by E6APΔ495 is consistent with a model in which the truncation competitively disrupts an intrinsic E6AP ligase wild-type oligomer that is required for activity, schematically illustrated in FIG. 2F. Overall, the data reveal that oligomerization of E6AP ligase is required for catalytic competence in polyubiquitin chain assembly. The similarities in $K_i$ values between the E6APΔ495 and E6AP-HectC820A proteins suggest that the Hect domain and the targeting regions both contribute to oligomerization.

Example 5

E6AP-catalyzed $^{125}$I-Ubiquitin Conjugation Assay: The E3 ligase activity of recombinant E6AP ligase was quantitated in kinetic assays under initial velocity conditions (Ronchi et al., (2013) *J. Biol. Chem.* 288, 10349-10360, Ronchi & Haas (2012) *Methods Mol. Biol.* 832: 197-218). Rates of E6AP-catalyzed $^{125}$I-polyubiquitin chain formation were measured at 37° C. in incubations of 25-μl final volume containing 50 mM Tris-HCl (pH 7.5), 1 mM ATP, 10 mM MgCl2, 1 mM DTT, 10 mM creatine phosphate, 1 IU of creatine phosphokinase, 5 μM $^{125}$I-ubiquitin (approximately 1.5×10$^4$ cpm/pmol), 50 nM human Uba1, and the indicated concentrations of UbcH7 and E6AP ligase (Siepmann et al., (2003) *J. Biol. Chem.* 278: 9448-9457; Baboshina et al., (2001) J. Biol. Chem. 276: 39428-39437).

Reactions were initiated by the addition of $^{125}$I-ubiquitin. After 10-30 min, the reactions were quenched by the addition of 25 μl of 2×SDS sample buffer containing 0.3% (v/v) β-mercaptoethanol, and then the samples were heated to 100° C. for 3 min. The polyubiquitin conjugates were resolved from free $^{125}$I-ubiquitin by 12% (w/v) SDS-PAGE under reducing conditions at 4° C. and visualized by autoradiography of the dried gels.

Polyubiquitin chain formation was measured by excising lanes between the top of the resolving gel and the top of the stacker gel, representing anchored and free $^{125}$I-polyubiquitin chains, respectively, and quantitating associated $^{125}$I-ubiquitin by γ-counting. Absolute rates of $^{125}$I-polyubiquitin chain formation were calculated from the associated radioactivity and the corrected specific radioactivity for $^{125}$I-ubiquitin. Datum points represent single assay determinations, and complete data sets were evaluated by non-linear regression analysis using GraFit version 5.0 (Erithicus). Active Uba1, E2, and E6AP ligase were independently determined in parallel by their stoichiometric formation of $^{125}$I-ubiquitin thioester.

Example 6

Static Light-scattering Measurements: His$_6$-E6AP ligase after the His trap affinity purification step was further purified by FPLC using a Mono Q 5/50 column (Amersham Biosciences) equilibrated in 50 mM Tris-HCl (pH 7.5) and 1 mM DTT. Recombinant His$_6$-E6AP ligase eluted at 300 mM NaCl in a 0-500 mM gradient (16 mM/ml, 1 ml/min). The molecular weight of His$_6$-E6AP ligase was determined in solution at 37° C. by static light-scattering using a 235-DynaPro NanoStar laser light-scattering spectrometer at 663 nm wavelength (Wyatt Technology Corp.). Spectra were collected for 18 μM His$_6$-E6AP ligase in 50 mM Tris-HCl (pH 7.5) containing 200 mM NaCl. The effect of Ac-PheNH$_2$ on the molecular weight of His$_6$-E6AP ligase was determined in 50 mM Tris-HCl (pH 7.5) containing 200 mM NaCl, 16 μM His$_6$-E6AP ligase total protein, 61 mM Ac-PheNH$_2$, and 8% (v/v) carrier methanol. The molecular weight of E6AP ligase was also evaluated in reactions containing 0-350 μM Ac-NRIRMYSERRITVLYSL (SEQ ID NO: 1) in 50 mM Tris-HCl (pH 7.5), 250 mM NaCl, 1 mM DTT, and 17 μM His$_6$-E6AP. Data were analyzed with Dynamics® software at both default and maximum sensitivity to detect the presence of low concentrations of E6AP ligase oligomeric forms.

Example 7

Analysis of E6AP-Hect Interface Structure: The E6AP ligase Hect domain structure (PDB code 1 D5F) corresponding to the E6AP ligase trimer reported by Huang et al. ((1999) *Science* 286: 1321-1326) was analyzed using PISA (PDBePISA-EMBL-EBI (Protein Interfaces, Surfaces, and Assemblies)) (Krissinel & Henrick (2007) *J. Mol. Biol.* 372, 774-797). The Assemblies analysis predicted a strong interaction between subunits, and default conditions detected an average of 38 residues/subunit involved in surface interactions between adjacent subunits (Krissinel & Henrick (2007) *J. Mol. Biol.* 372, 774-797). All structural representations were generated with PyMOL (Schrödinger, LLC).

Example 8

Active E6AP ligase is an Oligomer: Resolution of bacterially-expressed protein by SDS-PAGE and visualization by Coomassie staining revealed a series of GST-associated bands in preparations ranging from a relative mobility of approximately 130 kDa for full-length protein, in agreement with the expected size of 125 kDa, to 25 kDa, representing the free GST moiety (FIG. 3A, left lane); however, only the band of highest relative molecular weight, corresponding to full-length GST-E6AP, formed a $^{125}$I-ubiquitin thioester (Ronchi et al., (2013) *J. Biol. Chem.* 288, 10349-10360). Because bacterially-expressed recombinant GST-E6AP ligase is isolated as a mixture of full-length and C-terminal truncations (FIG. 3A, left), the results of FIG. 2A-2E suggest that the kinetic studies likely underestimate the intrinsic k$_{cat}$ for the ligase due to the presence of endogenous GST-E6AP ligase fragments.

To test this, full-length E6AP ligase was cloned into a baculovirus expression system to yield greater than 95% full-length ligase. The resulting N-terminal His$_6$-E6AP ligase could be isolated from the medium without the marked fragmentation observed for bacterially expressed GST-E6AP ligase and exhibited a relative molecular mass of 100 kDa, corresponding to the predicted value for full-length protein (FIG. 3A, right). After purification, maintaining the protein in a low concentration of NaCl was essential to prevent protein precipitation upon removal of imidazole.

On a lower percentage SDS-polyacrylamide gel, the full-length affinity-purified band could be resolved into two closely migrating bands, only the slower migrating band of which could be detected on Western blots using anti-His$_6$ antibody compared with detection by anti-E6AP ligase antibody (FIG. 3B). A trace fragment band lacking the His$_6$ tag could also be detected by anti-E6AP ligase Western blot (FIG. 3B). Co-purification of E6AP ligase lacking the affinity tag with His$_6$-E6AP ligase is consistent with oligomerization of the enzyme indicated by the results of FIGS. 2A-2E.

Recombinant GST-E6AP ligase in preparations identical to that analyzed in FIG. 3A (left) exhibit hyperbolic kinetics for $^{125}$I-polyubiquitin chain formation with respect to [UbcH7]$_o$, from which values of K$_m$ and k$_{cat}$, the latter defined as V$_{max}$/[GST-E6AP]$_o$, could be determined. Baculoviral-expressed His$_6$-E6AP ligase also yielded hyperbolic kinetics for $^{125}$I-polyubiquitin chain formation with respect to [UbcH7]$_o$ from which the K$_m$ (46±7 nM) and k$_{cat}$ (0.63±0.03 s−1) could be determined by nonlinear hyperbolic regression analysis (Table 1).

That homogeneous full-length E6AP ligase exhibits a K$_m$ indistinguishable from that of the bacterial-expressed heterogeneous GST-E6AP ligase preparations, but a 20-fold higher k$_{cat}$ is consistent with a model for oligomerization. Similarly, GST-E6AP ligase Hect domain protein composed of residues 450-872 is capable of modest polyubiquitin chain formation and has an affinity for UbcH7~ubiquitin thioester (K$_m$=89±11 nM) that is slightly less than that of full-length E6AP ligase but a k$_{cat}$ that is 2000-fold lower (Table 1). In contrast, removing the GST moiety by in situ processing with thrombin prior to assay abrogates chain formation; however, the resulting Hect domain moiety catalyzes a slow rate of monoubiquitination, as noted previously.

The kinetics of Hect domain monoubiquitination follows hyperbolic kinetics with respect to [UbcH7]$_o$, and yields K$_m$ and k$_{cat}$ values similar to those of the unprocessed GST-Hect domain (Table 1). The results of Table 1 are not a consequence of differences in the amounts of active protein in the various preparations because in each case the ligase is quantitated by the functional assay of stoichiometric Hect domain~$^{125}$I-ubiquitin thioester formation. Therefore, polyubiquitin chain formation kinetics for the various forms of E6AP ligase (Table 1) and the effect of N-terminal truncation (FIGS. 2A-2E) are consistent with the catalytically active form of the enzyme existing as an oligomer.

Example 9

A Trimer is the Fully Active Form of E6AP: To test directly the ability of E6AP ligase to oligomerize, the solution molecular weight of wild-type $His_6$-E6AP ligase was determined by gel filtration chromatography (FIG. 4A). The relative molecular weight for E6AP, monitored by $^{125}$I-polyubiquitin chain formation under E3-limiting conditions, encompasses a peak centered at 190 kDa. This molecular weight is consistent with a stable dimer of 100-kDa subunits or less stable higher oligomers subject to dissociation by dilution as the complex passes through the column. To distinguish between the latter, a parallel sample was analyzed by static light-scattering, which does not involve sample dilution. Following Mono Q anion exchange chromatography to remove inactive high molecular weight aggregates, freshly prepared active $His_6$-E6AP ligase displayed a molecular mass of 283 kDa by static light-scattering that was consistent with a trimer (FIG. 4A). The low abundance higher molecular weight species of approximately 50 nm radius represents aggregates not completely removed by the Mono Q FPLC step. In parallel experiments, the molecular mass ranged from about 200 to about 400 kDa depending on protein concentration, pH, and ionic strength, consistent with equilibrium oligomerization of the 100-kDa monomer.

Figure 5A:
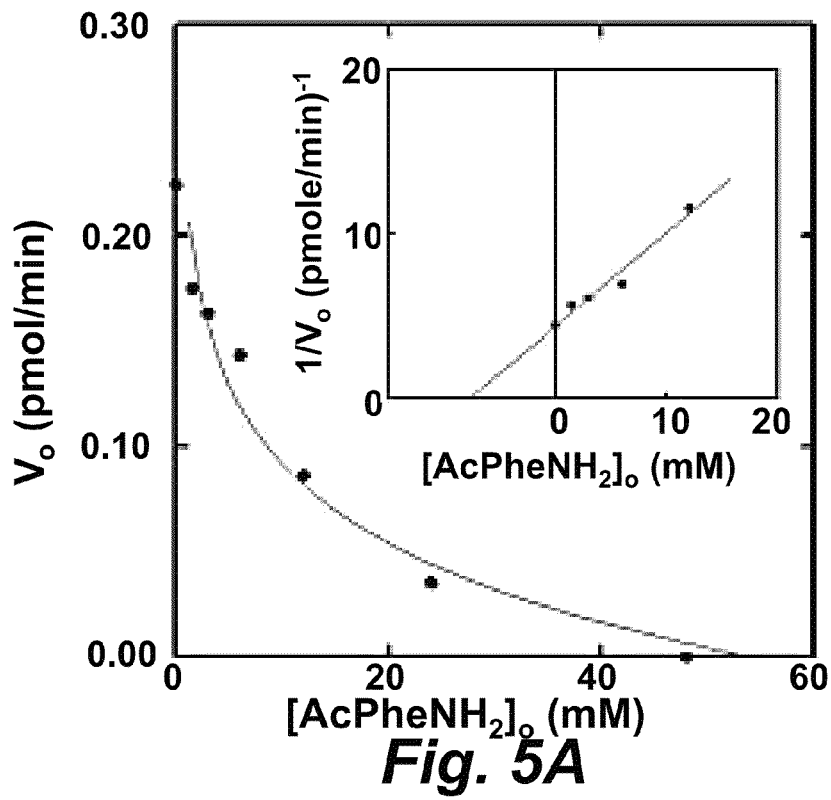
FIGS. 5A and 5B illustrate that active E6AP ligase is a trimer stabilized by $Phe^{727}$ interactions.
Figure 5B:
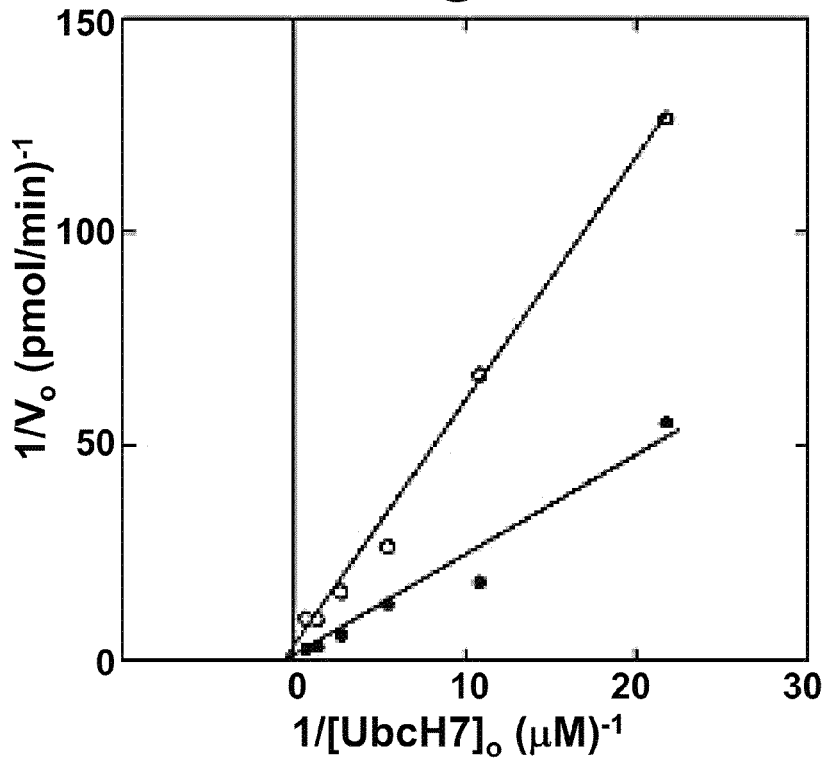

Wild type E6AP ligase is thought to exist as a monomer; however, the original publication reporting the structure of the isolated Hect domain also noted a trimeric structure that was proposed to arise from crystal packing interactions (Huang et al., (1999) *Science* 286: 1321-1326) (FIG. 5A). Based on the data of FIGS. 4A-4C and the requirement that E6AP-catalyzed polyubiquitin chain formation requires oligomerization, it is likely that the fully active form of the ligase is a trimer. The symmetric trimer (PDB code 1D5F) (Huang et al., (1999) *Science* 286: 1321-1326) buries an extensive combined surface area of 7508 Å comprising a large fraction of apolar residues at the subunit interfaces that represents a solvation free energy of −4.2 kcal/mol by PISA analysis (Krissinel & Henrick (2007) *J. Mol. Biol.* 372, 774-797) (FIG. 5A), corresponding to an apparent $K_d$ of 25 µM for E6AP ligase Hect subunit interactions without considering additional hydrogen bond or salt bridge interactions that are difficult mathematically to model due to uncertainties related to the actual microenvironments of the individual bonds. However, the predicted $K_d$ based on desolvation agrees with the empirical $K_i$ obtained with GST-HectC820A (31±4 µM) and HectC820A (27±9 µM) (FIG. 2D). The separation distance between N-terminal residues of the Hect domain subunits suggests that the N-terminal targeting domains of the subunits present on the full-length molecule would not hinder trimer formation (FIG. 5B).

As a trimer, the 1 DF5 structure reveals a number of radially symmetric subunit interactions. For example, the large N-terminal subdomain of the Hect domain contains a subset of conserved apolar residues at the subunit interface ($Ile^{600}$, $Tyr^{601}$, $Leu^{723}$, $Leu^{726}$, $Ile^{732}$, and $Leu^{735}$) that forms a hydrophobic pocket into which intercalates $Phe^{727}$ of the adjacent subunit in the trimer (Huang et al., (1999) *Science* 286: 1321-1326) (FIG. 5C), providing a stabilization of −2.13 kcal/mol by PISA analysis. Although there are other residues and surfaces contributing to stabilization of the trimer, intercalation of $Phe^{727}$ into the hydrophobic pocket appears to be of special importance because mutation of $Phe^{727}$ to alanine destabilizes trimeric E6AP ligase in favor of the monomer, the latter of which retains the ability to form a ubiquitin thioester intermediate (Huang et al., (1999) *Science* 286: 1321-1326).

The E6AP ligase catalytic cycle comprises a two-step mechanism involving rapid transthiolation of activated ubiquitin from the cognate E2~-ubiquitin co-substrate to the Hect $Cys^{820}$ active site residue followed by rate-limiting chain elongation to form the polyubiquitin degradation signal. Because of this, $Cys^{820}$-thioester formation is an insensitive measure of E6AP ligase catalytic competence, accounting for the reported inconsistencies between known loss-of-function mutations in Angelman syndrome and retention of the ability of the enzyme to form an active $Cys^{820}$-linked thioester to ubiquitin (Cooper et al., (2004) *J. Biol. Chem.* 279: 41208-41217). To re-examine this point, $Phe^{727}$ was mutated to aspartic acid to more efficiently disrupt trimer formation. The E6APF727D mutation significantly reduces the ability of the enzyme to form polyubiquitin chains, as shown by the 62-fold decrease in $k_{cat}$ without significant effect on the $K_m$ for UbcH7~$^{125}$I-ubiquitin thioester binding (Table 2) or end point $Cys^{820}$ thioester formation (not shown), the latter as noted previously.

Additional evidence that trimeric E6AP ligase represents the functional form of the enzyme comes from the effect of $Ac-PheNH_2$ as a mimic of $Phe^{727}$. The addition of $Ac-PheNH_2$ to $His_6$-E6AP ligase results in quantitative dissociation of the oligomer to a 104 kDa peak, in agreement with the expected molecular weight of the monomer (FIG. 4C). This observation is consistent with substitution of Ac-$PheNH_2$ into the conserved hydrophobic pocket to disrupt the radially symmetric subunit interactions stabilizing the trimer and is accompanied by quantitative inhibition of $^{125}$I-polyubiquitin chain formation, as shown in FIG. 5D).

The dependence of initial velocity on $[UbcH7]_o$ in the absence or presence of 44 mM $Ac-PheNH_2$ shows the amino acid derivative to be a non-competitive inhibitor with a $K_i=12\pm3$ mM, which is in agreement with the calculated $K_d$ of 27 mM predicted from the −2.13 kcal/mol stabilization predicted by PISA. In addition, non-competitive inhibition by $Ac-PheNH_2$ is consistent with that predicted for an effect on subunit dissociation (FIG. 5B) and the observed consequence of the E6APF727D mutation (Table 2). Although $Ac-PheNH_2$ can potentially interact with other regions comprising the interface of full-length $His_6$-E6AP, the linearity of the double reciprocal plots for FIGS. 5A (inset) and 5B, are consistent with binding at a single homogeneous site, presumably the buried conserved hydrophobic pocket.

Example 10

A Conserved α-Helix Blocks E6AP ligase Trimer Formation: Hect domains WWP1 (PDB code 1ND7), Smurf2 (PDB code 1ZVD), HuWE1 (PDB code 3H1D), Nedd4-1 (PDB code 2XBB), Nedd4-2 (PDB code 2XBF), and yeast RSP5 (PDB codes 3OLM and 4LCD), provides no other instance of trimer formation. However, these Hect domain structures contain additional sequence N-terminal to the truncation site for E6AP ligase at $Asn^{497}$ that is not present in the E6AP ligase structure (Huang et al., (1999) *Science* 286: 1321-

1326). Immediately N-terminal to Asn$^{497}$ is an extensive amphipathic α-helix corresponding to residues 474-490 that is relatively conserved among the Hect ligases, contributes to domain stability, and correlates with reduced autoubiquitination and target protein conjugation (Pandya et al., (2010) *J. Biol. Chem.* 285: 5664-5673; Ogunjimi et al., (2005) *Mol. Cell* 19: 297-308). In all of the Hect domain structures containing the additional segment, the hydrophobic face of the amphipathic N-terminal α-helix binds to the hydrophobic pocket normally occupied by Phe$^{727}$ in the trimeric E6AP ligase structure (Verdecia et al., (2003) *Mol. Cell* 11: 249-259; Ogunjimi et al., (2010) *J. Biol. Chem.* 285: 6308-6315; Pandya et al., (2010) *J. Biol. Chem.* 285: 5664-5673; Maspero et al., (2011) *EMBO Rep.* 12: 342-349; Kamadurai et al., (2009) *Mol. Cell* 36: 1095-1102). It is contemplated, therefore, that the interaction of the α-helix can block oligomerization, accounting for the observed reduction in ligase activity because we here demonstrate that trimer formation is required for polyubiquitin chain assembly.

To address the role of the N-terminal α-helix, the initial rate of polyubiquitin chain formation was analyzed in the absence or presence of an N-terminal blocked Ac-NRIRMY-SERRITVLYSL peptide (SEQ ID NO: 1) corresponding to residues 474-490 of E6AP ligase isoform 1 to mimic the proposed effect of this segment (FIGS. 6A-6C). With increasing concentrations of the peptide, the initial rate of E6AP-catalyzed chain formation decreased with a hyperbolic dependence (FIG. 6A), as shown by the linearity of the corresponding semi-reciprocal plot, yielding an apparent $K_i$ of 22±2 μM (FIG. 6A, inset). When the concentration dependence of the initial rate for polyubiquitin chain formation on [UbcH7]$_o$ was examined in the absence or presence of 32 μm peptide, the isolated α-helix was a classic non-competitive inhibitor (FIG. 6B).

The empirical $K_i$ likely underestimates the intrinsic affinity of the wild-type N-terminal α-helix because the isolated peptide is unlikely quantitatively to maintain the secondary structure of the intact protein. Nonetheless, observation of non-competitive inhibition is consistent with the peptide blocking trimerization of E6AP ligase in a manner analogous to Ac-PheNH$_2$ (FIGS. 5A and 5B) and mutation of Phe$^{727}$ (Table 2). Further, the peptide promotes dissociation of the E6AP ligase oligomer when analyzed by static light-scattering (FIG. 6C).

Example 11

Identification of Additional Subunit Interface Residues Affecting E6AP ligase Catalytic Activity: The present data and recent insights into the properties of protein subunit interfaces support the E6AP ligase trimer as the catalytically relevant structure (Levy & Teichmann (2013) *Prog. Mol. Biol. Transl. Sci.* 117: 25-51; Perica et al., (2012) *Proc. Natl. Acad. Sci. U.S.A.* 109: 8127-8132). The interaction surfaces of the trimer were analyzed by PISA to define other side chain interactions contributing to stability beyond that of Phe$^{727}$. A comprehensive sequence alignment of human Hect ligases cross-referenced to the results of PISA identified a number of conserved positions that appear potentially critical, including the hydrophobic pocket residues into which Phe$^{727}$ intercalates. Several of these residues represent or are adjacent to documented Angelman syndrome point mutations. In particular, Tyr$^{533}$ is an Angelman syndrome mutation site and which participates in a pattern of side chain interactions between subunits (Fang et al., (1999) *Hum. Mol. Genet.* 8: 129-135). Tyr$^{533}$ also exists in the region of subunit interface recently suggested by Chan et al. to be sensitive to cAbI-dependent regulation by phosphorylation of Tyr636 (Chan et al., (2013) *Biochemistry* 52: 3119-3129).

Figure 7A:
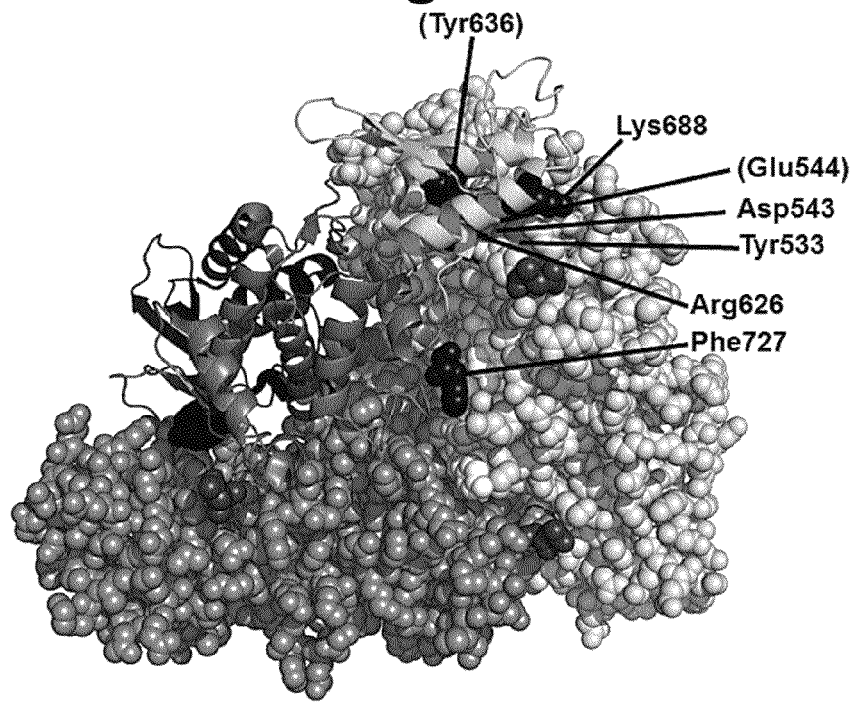
FIGS. 7A-7C illustrate selected side-chain interactions within the E6AP ligase Hect domain trimer.
Figure 7B:
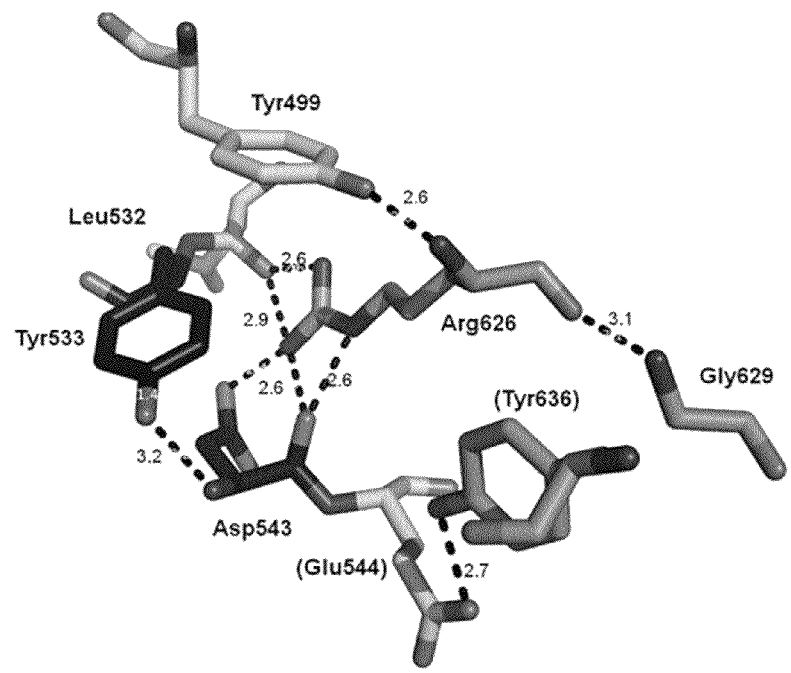
Figure 7C:
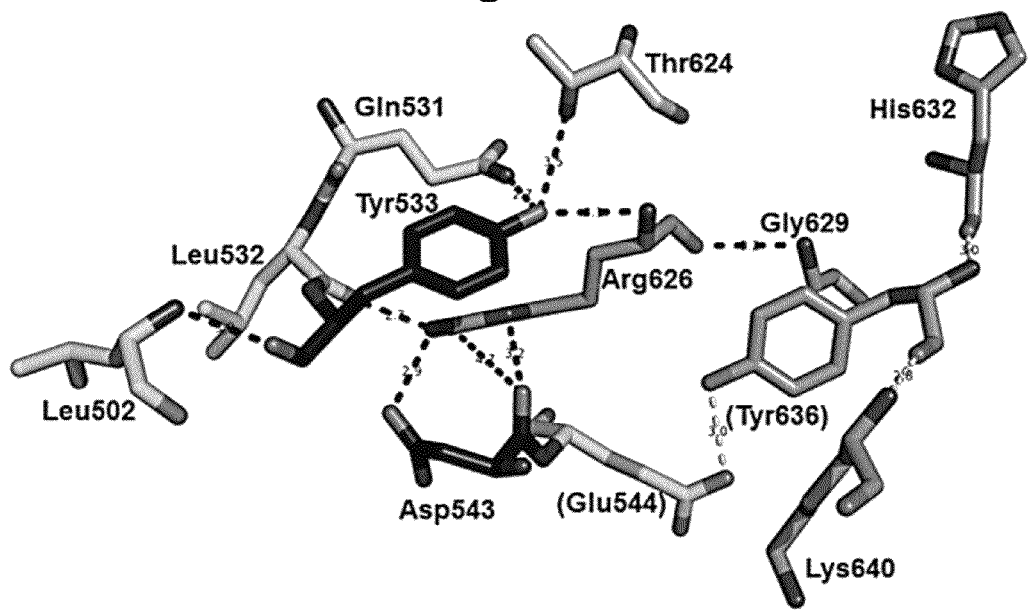

For two of the subunits in the trimer structure, the side chain phenolic group of Tyr$^{533}$ hydrogen bonds with the amide hydrogen of Asp$^{543}$ present on the same polypeptide chain (FIG. 7B), whereas for the third subunit, Tyr$^{533}$ is rotated 60° and hydrogen-bonds to the amide hydrogens of Arg$^{626}$ and Thr$^{624}$ on the adjacent chain (FIG. 7C). More important, for all three subunits, the side chain carboxyl and amide carbonyl groups of Asp$^{543}$ hydrogen-bond to the side chain guanidinium of Arg$^{626}$ (FIGS. 7B and 7C). Tyrosine$^{533}$ and Asp$^{543}$ reside within the Hect large N-terminal subdomain, whereas Arg$^{626}$ is in the small N-terminal subdomain of the adjacent subunit, so that the three residues constitute a radial symmetric pattern of subunit interactions.

Each of the residues was independently mutated to alanine and examined for the effect on the kinetics for $^{125}$I-polyubiquitin chain formation with respect to [UbcH7]$_o$ under rigorously E3-limiting conditions (Table 2). As a control, Lys688, a residue present on the same small N-terminal subdomain interface as Arg$^{626}$, which PISA analysis indicates hydrogen-bonds to the side chain of Glu535 in the adjacent subunit was also mutated. All four mutants formed $^{125}$I-ubiquitin thioesters to Cys$^{820}$ with kinetics qualitatively similar to that of wild-type enzyme in short term incubations (Ronchi et al., (2013) *J. Biol. Chem.* 288, 10349-10360).

Mutation of Lys$^{688}$ did not have a significant effect on the kinetics of $^{125}$I-polyubiquitin chain assembly (Table 2). However, given the large number of predicted subunit interactions stabilizing the trimer, abrogating a single site might not be expected a priori to have a large effect except for those interactions particularly critical for structural integrity. In contrast to the effect of mutating Tyr$^{688}$, mutation of Tyr$^{533}$ decreased $k_{cat}$ 10-fold but had no effect on the $K_m$ for UbcH7~ubiquitin binding (Table 2). Similarly, mutation of Arg$^{626}$ decreased $k_{cat}$ 155-fold but had little effect on $K_m$ (Table 2). Both of the latter mutants are consistent with an effect on oligomerization, given their position within the trimer structure and distance from the active site Cys$^{820}$ as well as the fact that neither mutation alters the ability of E6AP ligase to bind its UbcH7~ubiquitin thioester substrate. Mutation of Asp$^{543}$ similarly reduced $k_{cat}$ 8-fold but additionally increased Km significantly (Table 2). Together with the effects of Tyr$^{636}$ phosphorylation (Chan et al., (2013) *Biochemistry* 52: 3119-3129), the consequences of these point mutants reveal complex interactions affecting the catalytic function of E6AP.

Example 12

E6 Protein Enhances E6AP ligase Polyubiquitin Chain Synthesis: HPV16 E6 protein is thought to promote viral replication and host epithelial cell transformation by serving as an E6AP ligase adapter to target the p53 tumor suppressor protein for 26S proteasome-dependent degradation. Recent structural work demonstrates that the 158-amino acid E6 viral protein contains structurally related N-terminal and C-terminal $Zn^{2+}$-binding domains connected by a linker polypeptide. The C-terminal domain binds p53 but also shows limited interaction with E6AP. In contrast, the N-terminal domain exhibits significant affinity for E6AP ligase through binding to a canonical LXXLL motif on the ligase and is additionally responsible for E6 protein self-association, accounting for the observation that the complex between E6 protein and p53 consists of a p53 tetramer and an E6 dimer. As expected, disrupting the dimerization interface by mutation inhibits E6-dependent p53 conjugation by E6AP ligase but also enhances E6 protein solubility, which probably relates to earlier observations that ectopic expression of E6 protein stimulates autoubiquitination and subsequent E6AP ligase degradation in vivo.

Because the trimer is the presumed catalytically fully active form of E6AP, it was contemplated that the effect of E6 protein on E6AP ligase turnover (Dai et al., (2010) *Cancer Res.* 70: 2951-2961) and the stabilization of p53 when the E6 dimerization interface is disrupted might reflect the ability of the viral protein to promote E6AP ligase oligomerization.

FIG. 8A shows the effect of recombinant E6 protein on the $[UbcH7]_o$, dependence of E6AP-catalyzed $^{125}$I-polyubiquitin chain formation. Initial rates of chain formation were enhanced in the presence of E6 protein, with the $k_{cat}$ increasing from $0.057\pm0.029$ s$^{-1}$ in the absence of E6 protein to $0.81\pm0.045$ s$^{-1}$ in its presence. The corresponding double reciprocal plot shows E6 protein to be a non-essential activator, exhibiting a $k_{cat}$ effect (inset), and with a $K_d$ for E6 binding corresponding to 1.5 nM. These results are consistent with a mechanism in which the E6 dimer promotes oligomerization of E6AP ligase to the catalytically competent trimer through binding to a site distinct from the catalytic site, presumably the leucine-rich LXXLL motif (Chen et al., (1998) *J. Biol. Chem.* 273: 13537-13544; Elston et al., (1998) *J. Gen. Virol.* 79: 371-374; Be et al., (2001) *Biochemistry* 40: 1293-1299).

Figure 8B:
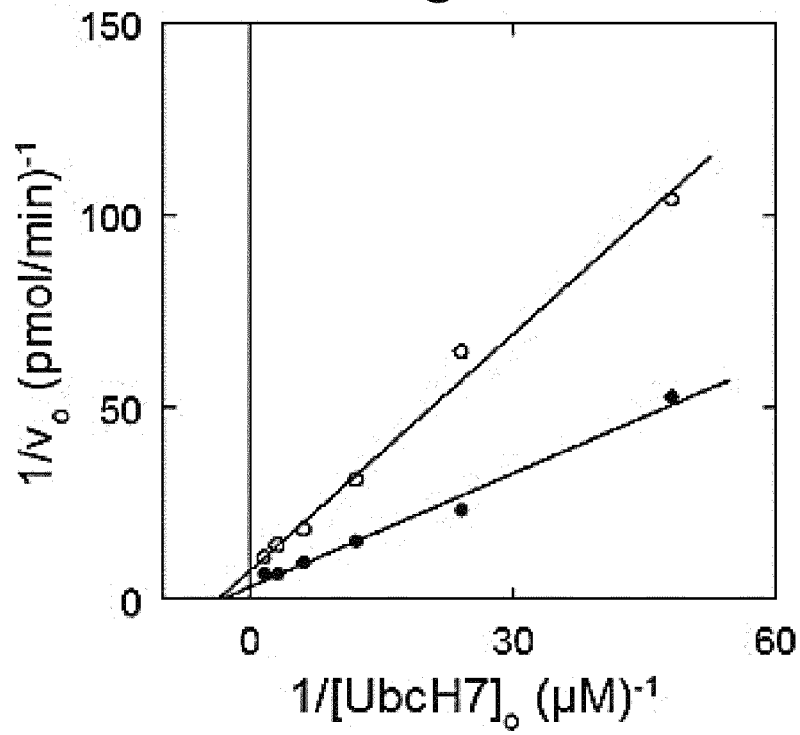
Figure 8C:
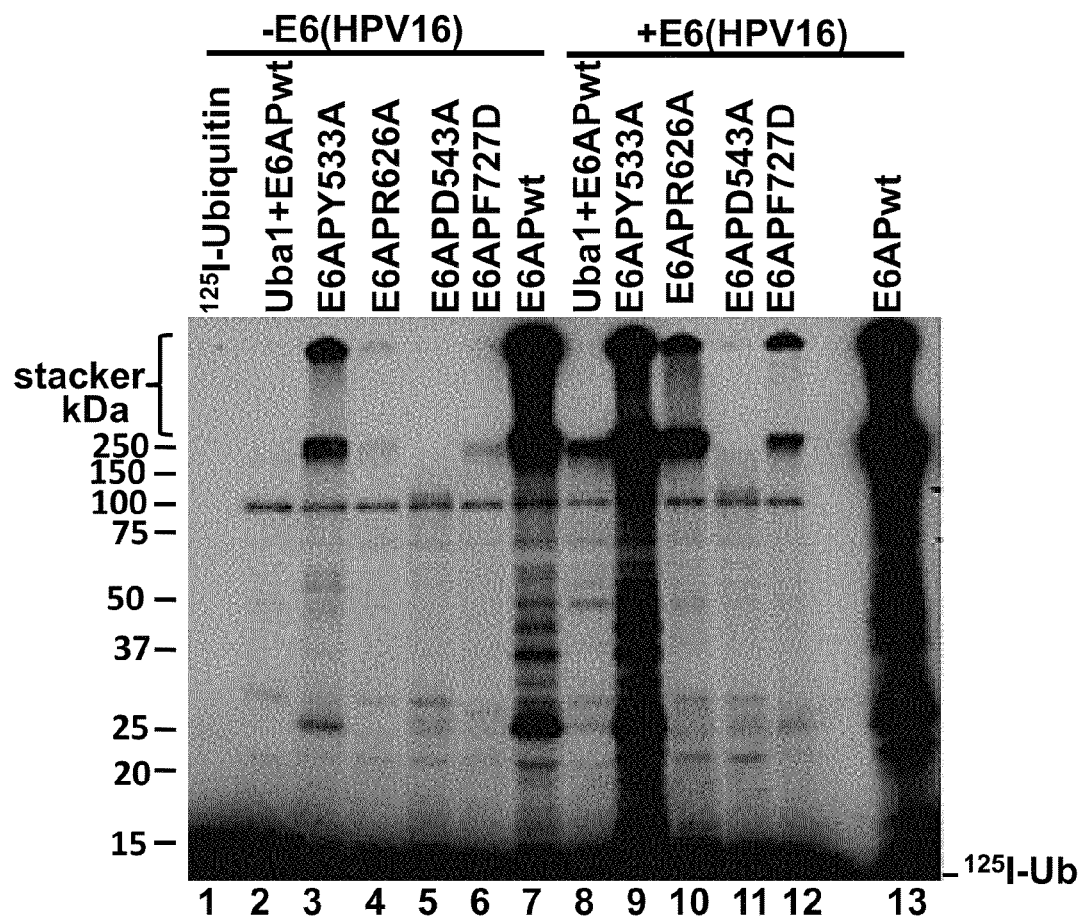
Figure 8D:
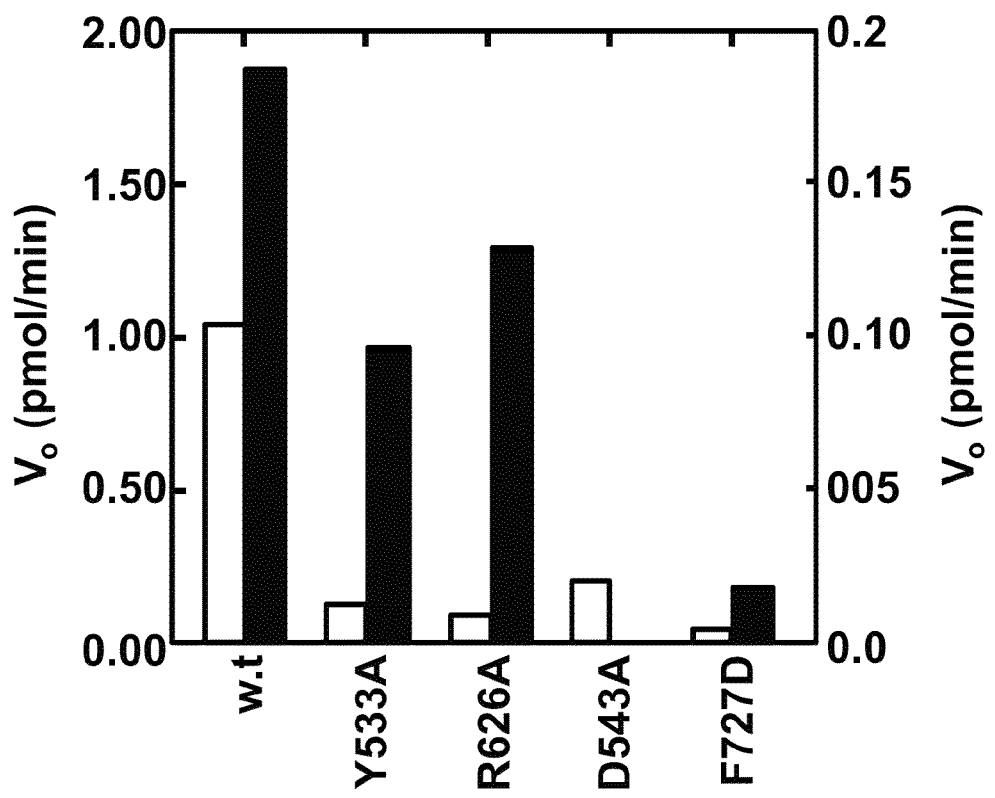

Although the N-terminal domain contains both the dimerization interface and the LXXLL association motif, the recombinant E6(HPV16)Δ91 N-terminal domain encompassing residues 1-91 inhibits E6AP-catalyzed polyubiquitin chain formation with a hyperbolic concentration dependence (apparent Ki=4 µM; not shown) and displays non-competitive inhibition with respect to $[UbcH7]_o$, corresponding to $K_i$=6 µM (FIG. 8B). Similarly, the recombinant E6(HPV16)Ct C-terminal domain encompassing residues 89-158 is a non-competitive inhibitor of E6AP ligase with respect to $[UbcH7]_o$ corresponding to $K_i$=4 µM. Collectively, the results indicate that both E6 domains bind E6AP, presumably at different sites, to promote oligomerization of full-length E6AP. This conclusion supports earlier empirical binding evidence demonstrating interaction of each domain with E6AP.

Because full-length E6 protein acts as a non-essential activator by promoting E6AP ligase trimer formation, it was determined whether the viral protein could rescue the loss-of-function phenotype displayed by the E6APF727D point mutant. The addition of 20 nM E6 protein significantly enhanced the initial rate of $^{125}$I-polyubiquitin chain formation for wild-type protein (FIG. 8C, lanes 7 and 13) as seen in FIG. 8A and E6APF727D (FIG. 8C, lanes 6 and 12). Similar rescue of $^{125}$I-polyubiquitin chain formation was observed in an 8-fold increase in rate for E6APY533A (FIG. 8C, lanes 3 and 9) and a 13-fold increase in rate for E6APR626A (FIG. 8C, lanes 4 and 10). In contrast, no enhancement in rate was observed for the E6APD543A point mutant (FIG. 8C, lanes 5 and 11). These results are consistent with E6 rescuing the loss-of-function phenotype for selected point mutants by promoting oligomerization.

What is claimed:

1. A method of modulating the activity of a ubiquitin-protein E3 ligase comprising the step of inhibiting the formation of an E6-Associated Protein (E6AP) polypeptide trimer by contacting the E6AP polypeptide with an agent that binds to the E6AP polypeptide, wherein the agent is N-acetyl-L-phenylalanylamide, and thereby reducing the generation of a ubiquitin-protein E3 lipase activity.

2. The method of claim 1, wherein the E6AP is encoded by the UBE3A gene.

3. The method of clam 1, wherein the step of generating a E6-Associated Protein (E6AP) polypeptide trimer is in a cell or in vitro.

* * * * *